(12) United States Patent
Saltiel et al.

(10) Patent No.: US 10,245,255 B2
(45) Date of Patent: Apr. 2, 2019

(54) COMPOSITIONS AND METHODS FOR THE TREATMENT OF OBESITY AND RELATED DISORDERS

(75) Inventors: Alan R. Saltiel, Ann Arbor, MI (US); Stuart Decker, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1143 days.

(21) Appl. No.: 13/396,320

(22) Filed: Feb. 14, 2012

(65) Prior Publication Data

US 2012/0208836 A1 Aug. 16, 2012

Related U.S. Application Data

(60) Provisional application No. 61/442,558, filed on Feb. 14, 2011.

(51) Int. Cl.
*A61K 31/44* (2006.01)
*A61K 31/436* (2006.01)

(52) U.S. Cl.
CPC .................. *A61K 31/436* (2013.01)

(58) Field of Classification Search
CPC .................................. A61K 31/4353
USPC ...................................... 514/291
See application file for complete search history.

(56) References Cited

U.S. PATENT DOCUMENTS

| | | |
|---|---|---|
| 4,108,663 A | 8/1978 | Okazaki et al. |
| 4,143,042 A | 3/1979 | Nohara |
| 4,192,749 A | 3/1980 | Jackson |
| 4,299,963 A | 11/1981 | Nohara et al. |
| 4,657,760 A | 4/1987 | Kung |
| 4,683,195 A | 7/1987 | Mullis |
| 4,683,202 A | 7/1987 | Mullis |
| 4,728,509 A | 3/1988 | Shimizu et al. |
| 4,800,159 A | 1/1989 | Mullis |
| 4,965,188 A | 10/1990 | Mullis |
| 5,130,238 A | 7/1992 | Malek |
| 5,206,344 A | 4/1993 | Katre |
| 5,223,409 A | 6/1993 | Ladner |

(Continued)

FOREIGN PATENT DOCUMENTS

| | | |
|---|---|---|
| EP | 0684315 | 11/1995 |
| JP | 2963496 | 10/1999 |

(Continued)

OTHER PUBLICATIONS

Bertola, et al., PloS One, Oct. 2010, vol. 5, Issue 10, p. e13577.*

(Continued)

*Primary Examiner* — Shengjun Wang
(74) *Attorney, Agent, or Firm* — Casmir Jones S.C.; Thomas Isenbarger

(57) ABSTRACT

Provided herein are compositions and methods for the treatment of obesity and related disorders, including, but not limited to insulin resistance, diabetes, and hepatic steatosis. For example, in some embodiments, pharmaceutically acceptable compositions and methods are provided employing amlexanox, a derivative thereof, or a pharmaceutically acceptable salt thereof, alone or in combination with other agents and/or medical interventions, for the treatment, prevention, and management of such diseases and conditions.

13 Claims, 30 Drawing Sheets

(56) References Cited

U.S. PATENT DOCUMENTS

| | | | |
|---|---|---|---|
| 5,225,212 A | 7/1993 | Martin | |
| 5,225,326 A | 7/1993 | Bresser | |
| 5,270,184 A | 12/1993 | Walker | |
| 5,283,174 A | 2/1994 | Arnold, Jr. | |
| 5,362,737 A | 11/1994 | Vora et al. | |
| 5,399,491 A | 3/1995 | Kacian | |
| 5,455,166 A | 10/1995 | Walker | |
| 5,480,784 A | 1/1996 | Kacian | |
| 5,545,524 A | 8/1996 | Trent | |
| 5,641,673 A | 6/1997 | Haseloff | |
| 5,710,029 A | 1/1998 | Ryder | |
| 5,814,447 A | 9/1998 | Ishiguro | |
| 5,824,518 A | 10/1998 | Kacian | |
| 5,925,517 A | 7/1999 | Tyagi | |
| 5,928,862 A | 7/1999 | Morrison | |
| 5,981,180 A | 11/1999 | Chandler | |
| 6,074,822 A | 6/2000 | Henry | |
| 6,121,489 A | 9/2000 | Dorner | |
| 6,150,097 A | 11/2000 | Tyagi | |
| 6,200,763 B1 | 3/2001 | Craig et al. | |
| 6,221,335 B1 | 4/2001 | Foster | |
| 6,291,491 B1 | 9/2001 | Weber et al. | |
| 6,303,305 B1 | 10/2001 | Wittwer | |
| 6,309,863 B1 | 10/2001 | Anderson | |
| 6,358,945 B1* | 3/2002 | Breitfelder | C07D 213/38 514/227.8 |
| 6,534,274 B2 | 3/2003 | Becker | |
| 6,541,205 B1 | 4/2003 | Yokoyama | |
| 6,566,354 B1 | 5/2003 | Rose et al. | |
| 6,573,043 B1 | 6/2003 | Cohen | |
| 6,603,008 B1 | 8/2003 | Ando et al. | |
| 6,630,312 B2 | 10/2003 | Shoelson | |
| 6,673,908 B1* | 1/2004 | Stanton, Jr. | C07K 14/7151 435/6.16 |
| 6,758,848 B2 | 7/2004 | Burbank | |
| 6,924,361 B1 | 8/2005 | Laudano | |
| 7,049,151 B2 | 5/2006 | Nguyen | |
| 7,085,439 B2 | 8/2006 | Andrieu | |
| 7,374,885 B2 | 5/2008 | Becker | |
| 8,299,084 B2 | 10/2012 | Rao et al. | |
| 8,445,679 B2 | 5/2013 | Wang et al. | |
| 8,946,424 B2 | 2/2015 | Saltiel et al. | |
| 9,394,303 B2 | 7/2016 | Nikolovska-Coleska et al. | |
| 9,486,422 B2 | 11/2016 | Nikolovska-Coleska et al. | |
| 2002/0103219 A1* | 8/2002 | Jacob | A61K 9/006 514/291 |
| 2003/0064408 A1 | 4/2003 | Cimbora | |
| 2003/0105086 A1 | 6/2003 | Michaelis et al. | |
| 2003/0124178 A1 | 7/2003 | Haley | |
| 2005/0042638 A1 | 2/2005 | Arnold, Jr. | |
| 2005/0197333 A1 | 9/2005 | Van Duzer et al. | |
| 2005/0261262 A1 | 11/2005 | Ma et al. | |
| 2005/0282818 A1 | 12/2005 | Ramesh | |
| 2006/0004003 A1 | 1/2006 | Abe et al. | |
| 2006/0094682 A1 | 5/2006 | Westwick et al. | |
| 2007/0060595 A1 | 3/2007 | Yoshizawa et al. | |
| 2007/0135473 A1 | 6/2007 | Alexandre et al. | |
| 2007/0149519 A1 | 6/2007 | Bamborough | |
| 2007/0203236 A1 | 8/2007 | Smith | |
| 2009/0054402 A1 | 2/2009 | Wang et al. | |
| 2009/0143373 A1 | 6/2009 | Ding et al. | |
| 2009/0196912 A1 | 8/2009 | Eickhoff | |
| 2009/0304714 A1 | 12/2009 | Saltiel et al. | |
| 2010/0009934 A1 | 1/2010 | Rickles et al. | |
| 2010/0167989 A1 | 7/2010 | Grant | |
| 2010/0184783 A1* | 7/2010 | Raud | A61K 31/167 514/259.41 |
| 2010/0256141 A1 | 10/2010 | Nemecek et al. | |
| 2012/0125325 A1 | 5/2012 | Bannister et al. | |
| 2012/0149693 A1* | 6/2012 | Booth | A61K 31/13 514/227.5 |
| 2012/0208836 A1 | 8/2012 | Saltiel et al. | |
| 2013/0030007 A1* | 1/2013 | Penninger et al. | 514/254.02 |
| 2015/0224089 A1 | 8/2015 | Saltiel et al. | |
| 2016/0060271 A1 | 3/2016 | Saltiel et al. | |
| 2016/0251366 A1 | 9/2016 | Saltiel et al. | |

FOREIGN PATENT DOCUMENTS

| | | |
|---|---|---|
| WO | 1997/049420 A1 | 12/1997 |
| WO | WO2004/022580 | 3/2004 |
| WO | WO2004/097009 | 11/2004 |
| WO | WO2005/075465 | 8/2005 |
| WO | WO2009/120801 | 10/2009 |
| WO | WO2009/149192 | 12/2009 |
| WO | WO2009/150614 | 12/2009 |
| WO | WO2010/005534 | 1/2010 |
| WO | WO2010/080478 | 7/2010 |
| WO | WO2010/102286 | 9/2010 |
| WO | 2010139985 A1 | 12/2010 |
| WO | WO2010/151799 | 12/2010 |
| WO | WO2012/016930 | 2/2012 |
| WO | WO2012/112558 | 8/2012 |
| WO | WO2012/178036 | 12/2012 |
| WO | WO2013/039988 | 3/2013 |
| WO | WO2013/052943 | 4/2013 |
| WO | WO2013/086415 | 6/2013 |
| WO | WO2014/111957 | 7/2014 |
| WO | WO2015/119624 | 8/2015 |
| WO | WO2015/153959 | 10/2015 |

OTHER PUBLICATIONS

Sawhney et al., "Bioerodible hydrogels based on photopolymerized poly(ethylene glycol)-co-poly(.alpha.-hydroxy acid) diacrylate macromers." Macromolecules 1993, 26(4): 581-587.

Chiang et al., "The protein kinase IKKepsilon regulates energy balance in obese mice." Cell. Sep. 4, 2009; 138(5):961-75.

Norris et al., "Muscle-specific PPARgamma-deficient mice develop increased adiposity and insulin resistance but respond to thiazolidinediones." J Clin Invest. Aug. 2003; 112(4):608-18.

Dandona et al., "Inflammation: the link between insulin resistance, obesity and diabetes." Trends Immunol. Jan. 2004; 25(1):4-7.

Bayard et al., "Nonalcoholic Fatty Liver Disease" American Family Physician, Jun. 1, 2006, 73(11):1961-1968.

Carey & Kingwell, "Novel Pharmacological approaches to combat obesity and insulin resistance: targeting skeletal muscle with 'exercise mimetics'." Diabetologia 2009, 52:2015-2026.

Ezquerra et al: "Obesity, MetabolicSyndrome, and Diabetes: Cardiovascular Implications and Therapy" Rev Esp Cardiol. Jul. 2008, 61(7):752-764.

Fulop et al., "The metabolic syndrome" Pathologie Biologie 2006, 54:375-386.

Khandwala et al., "5% amlexanox oral paste, a new treatment for recurrent minor aphthous ulcers II: Pharmacokinetics and demonstration of clinical safety." Oral Surgery Oral Medicine Oral Pathology Feb. 1997, 83(2):231-8.

Krawczyk et al., "Nonalcoholic fatty liver disease." Best Practice & Research Clinical Gastroenterology 2010, 24:695-708.

Remington's pharmaceutical sciences, 17th ed. Edited by Alfonso R. Gennaro. Mack Publishing Co. 1985.

Abad-Zapatero et al., Ligand efficiency indices as guideposts for drug discovery. Drug Discov Today 2005, 10(7):464-9.

Adli et al. IKK-i/IKKepsilon controls constitutive, cancer cell-associated NF-kappaB activity via regulation of Ser-536 p65/RelA phosphorylation. J Biol Chem. Sep. 15, 2006;281(37):26976-84.

Akira et al., Toll-like receptor signalling. Nat Rev Immunol. Jul. 2004;4(7):499-511.

Anderson & Young, Chapter 4. Quantitative Filter Hybridization. In Nucleic Acid Hybridization, eds Hames & Higgins, 1985. 41 pages.

Arkan et al., IKK-beta links inflammation to obesity-induced insulin resistance. Nature Medicine, 2005, 11:191-198.

Armoni et al., FOXO1 represses peroxisome proliferator-activated receptor-gamma1 and -gamma2 gene promoters in primary adipocytes. A novel paradigm to increase insulin sensitivity. J Biol Chem. Jul. 21, 2006;281(29):19881-91.

(56) References Cited

OTHER PUBLICATIONS

Baillie, The Use of Stable Isotopes in Pharmacological Research. Pharmacological Reviews 1981;33(2):81-132.
Bamborough et al., 5-(1H-Benzimidazol-1-yl)-3-alkoxy-2-thiophenecarbonitriles as potent, selective, inhibitors of IKK-epsilon kinase, Bioorganic and Medicinal Chemistry Letters, 2006, 16:6236-6240.
Bass, 2001, RNA interference. The short answer. Nature. May 24, 2001;411(6836):428-9.
Baumann et al., CAP defines a second signalling pathway required for insulin-stimulated glucose transport. Nature. Sep. 14, 2000;407(6801):202-7.
Berge et al., Pharmaceutical salts. J Pharm Sci. Jan. 1977;66(1):1-19.
Berger et al., Phosphodiesterase 3B is localized in caveolae and smooth ER in mouse hepatocytes and is important in the regulation of glucose and lipid metabolism. PLoS ONE, 2009, 4:e4671.
Bogan et al., Insulin-responsive compartments containing GLUT4 in 3T3-L1 and CHO cells: regulation by amino acid concentrations. Mol Cell Biol. Jul. 2001;21(14):4785-806.
Bodner Research Web, The Chemistry of the Halogens. © Apr. 2009. http://web.argive.org/web/20090414155348/http://chemed.chem.purdue.edu/genchem/topicreview/bg/ch10/group7.php. Retrieved Jun. 2, 2014, 11 pages.
Bradbury, Lipid metabolism and liver inflammation. I. Hepatic fatty acid uptake: possible role in steatosis. Am J Physiol Gastrointest Liver Physiol. Feb. 2006;290(2):G194-8.
Browne et al., Stable isotope techniques in early drug development: an economic evaluation. J Clin Pharmacol. Mar. 1998;38(3):213-20.
Buss et al., Constitutive and interleukin-1-inducible phosphorylation of p65 NF-{kappa}B at serine 536 is mediated by multiple protein kinases including I{kappa}B kinase (IKK)-{alpha}, IKK{beta}, IKK{epsilon}, TRAF family member-associated (TANK)-binding kinase 1 (TBK1), and an unknown kinase and couples p65 to TATA-binding protein-associated factor II31-mediated interleukin-8 transcription. J Biol Chem. Dec. 31, 2004;279(53):55633-43.
Cai et al., Local and systemic insulin resistance resulting from hepatic activation of IKK-beta and NF-kappaB. Nat Med. Feb. 2005;11(2):183-90.
Calay et al., Turning off the inflammatory, but not the metabolic, flames. Nature Medicine, 2013, 19:265-267.
Carell et al., A Novel Procedure for the Synthesis of Libraries Containing Small Organic Molecules. Angew Chem Int Ed Engl, 1994;33:2059-2061.
Cech, Ribozyme engineering. Curr Opin Struct Biol 1992;2:605-609.
Chen et al. Alterations in Hepatic Metabolism in fld Mice Reveal a Role for Lipin 1 in Regulating VLDL-Triacylglyceride Secretion. Arterioscler Thromb Vasc Biol 2008;28:1738-44.
Chen et al., Mcl-1 down-regulation potentiates ABT-737 lethality by cooperatively inducing Bak activation and Bax translocation. Cancer Res. Jan. 15, 2007;67(2):782-91.
Cho et al., An Unnatural Biopolymer. Science 1993;261:1303-5.
Choi et al., Alterations in regulation of energy homeostasis in cyclic nucleotide phosphodiesterase 3B-null mice. The Journal of Clinical Investigation, 2006, 116:3240-3251.
Clark et al., Novel cross-talk within the IKK family controls innate immunity. Biochemical Journal, 2011, 434:93-104.
Clark et al., Use of the pharmacological inhibitor BX795 to study the regulation and physiological roles of TBK1 and IkappaB kinase epsilon: a distinct upstream kinase mediates Ser-172 phosphorylation and activation. The Journal of Biological Chemistry. 2009, 284:14136-14146.
Cole et al., The EBV-Hybridoma Technique and Its Application to Human Lung Cancer. Monoclonal Antibodies and Cancer Therapy 1985, pp. 77-96.
Coppack et al., In vivo regulation of lipolysis in humans. Journal of Lipid Research, 1994, 35:177-193.
Cull et al., Screening for receptor ligands using large libraries of peptides linked to the C terminus of the lac repressor. PNAS 1992;89:1865-1869.
Cwirla et al., Peptides on phage: A vast library of peptides for identifying ligands. PNAS 1990;87:6378-6382.
Czabotar et al., Structural insights into the degradation of Mcl-1 induced by BH3 domains. Proc Natl Acad Sci U S A 2007, 104:6217-22.
Dai et al., Synthesis of the parent and substituted tetracyclic ABCD ring cores of camptothecins via 1-(3-aryl-2-propynyl)-1,6-dihydro-6-oxo-2-pyridinecarbonitriles. Org Lett 2006, 8:4665-7.
Dash et al., Apogossypol derivative BI-97C1 (Sabutoclax) targeting Mcl-1 sensitizes prostate cancer cells to mda-7/IL-24-mediated toxicity. Proc Natl Acad Sci U S A. 2011, 108(21):8785-90.
Day et al., Solution structure of prosurvival Mcl-1 and characterization of its binding by proapoptotic BH3-only ligands. J Biol Chem. Feb. 11, 2005;280(6):4738-44.
Day et al., Structure of the BH3 domains from the p53-inducible BH3-only proteins Noxa and Puma in complex with Mcl-1. J Mol Biol. Jul. 25, 2008;380(5):958-71.
Degerman et al., From PDE3B to the regulation of energy homeostasis. Current Opinion in Pharmacology, 2011, 11:676-682.
Devlin Random Peptide Libraries: A Source of Specific Protein Binding Molecules. Science 1990;249:404-406.
Dewitt et al., "Diversomers": an approach to nonpeptide, nonoligomeric chemical diversity. Proc Natl Acad Sci U S A. Aug. 1, 1993;90(15):6909-13.
Dorwald, Side Reactions in Organic Synthesis, 2005, Wiley: VCH, Weinhelm. 37 pages.
Du et al., A dual-readout F2 assay that combines fluorescence resonance energy transfer and fluorescence polarization for monitoring bimolecular interactions. Assay Drug Dev Technol 2011, 9:382-93.
Dyck et al., Effects of deuterium substitution on the catabolism of beta-phenylethylamine: an in vivo study. J Neurochem. Feb. 1986;46(2):399-404.
Elbashir et al., Duplexes of 21-nucleotide RNAs mediate RNA interference in cultured mammalian cells. Nature 2001;411:494-8.
Ettmayer et al., Lessons learned from marketed and investigational prodrugs. J Med Chem. May 6, 2004;47(10):2393-404.
Festuccia et al., Control of brown adipose tissue glucose and lipid metabolism by PPARgamma. Frontiers in Endocrinology. 2011, 2:84. 6 pages.
Fitzgerald et al., IKKepsilon and TBK1 are essential components of the IRF3 signaling pathway. Nature Immunology,2003, 4:491-496.
Ganesan et al., Synthesis of unsymmetrical pyrazines by reaction of an oxadiazinone with enamines. Journal of Organic Chemistry 1993, 58:6155-6157.
Ghorbani et al., Appearance of brown adipocytes in white adipose tissue during CL 316,243-induced reversal of obesity and diabetes in Zucker fa/fa rats. Int J Obes Relat Metab Disord. Jun. 1997;21(6):465-75.
Green et al., Stimulation of lipolysis by tumor necrosis factor-alpha in 3T3-L1 adipocytes is glucose dependent: implications for long-term regulation of lipolysis. Diabetes, 2004, 53:74-81.
Gregor et al., Inflammatory mechanisms in obesity. Annual Review of Immunology, 2011, 29:415-445.
Greig et al., Development and characterization of biphenylsulfonamides as novel inhibitors of bone resorption. J Med Chem 2006, 49:7487-92.
Griffiths et al., Cell damage-induced conformational changes of the pro-apoptotic protein Bak in vivo precede the onset of apoptosis. J Cell Biol. Mar. 1999 8;144(5):903-1.
Guoan et al., Adenovirus-mediated siRNA targeting Mcl-1 gene increases radiosensitivity of pancreatic carcinoma cells in vitro and in vivo. Surgery. Apr. 2010;147(4):553-61.
Hacker et al., Regulation and function of IKK and IKK-related kinases. Science's STKE, 2006, 2006(357):re13.
Hajduk, Fragment-based drug design: how big is too big? J. Med Chem 2006, 49:6972-6.
Han et al., Targeted prodrug design to optimize drug delivery. AAPS PharmSci. 2000;2(1):E6.

(56) References Cited

OTHER PUBLICATIONS

Hanahan et al., The hallmarks of cancer. Cell. Jan. 7, 2000;100(1):57-70.
Handbook of Pharmaceutical Salts, Properties, Selection, and Use, Stahl and Wermuth eds. 2002.
Hemmi et al., The roles of two IkappaB kinase-related kinases in lipopolysaccharide and double stranded RNA signaling and viral Infection. The Journal of Experimental Medicine, 2004, 199:1641-1650.
Hotamisligil, Inflammation and metabolic disorders. Nature, 2006, 444:860-867.
Huang et al., BH3 mimetic ABT-737 potentiates TRAIL-mediated apoptotic signaling by unsequestering Bim and Bak in human pancreatic cancer cells. Cancer Res. Apr. 15, 2008;68(8):2944-51.
Ikeda et al., Involvement of the ubiquitin-like domain of TBK1/IKK-i kinases in regulation of IFN-inducible genes. The EMBO Journal, 2007, 26:3451-3462.
Kishore et al., IKK-i and TBK-1 are enzymatically distinct from the homologous enzyme IKK-2: comparative analysis of recombinant human IKK-i, TBK-1, and IKK-2. J Biol Chem. Apr. 19, 2002;277(16):13840-7.
Kitamura et al., Insulin-induced phosphorylation and activation of cyclic nucleotide phosphodiesterase 3B by the serine-threonine kinase Akt. Molecular and Cellular Biology, 1999, 19:6286-6296.
Kuriki et al., Antiallergic action of amoxanox (AA-673), its main metabolite M-I and tranilast. Yakuri to Chiryo (1973-2000), 13(11):6435-46, 1985, Abstract Only.
Kurita et al., Efficient and convenient heterogeneous palladium-catalyzed regioselective deuteration at the benzylic position. Chem. Eur. J. 2008; 14(2):664-73.
Langin, Adipose tissue lipolysis as a metabolic pathway to define pharmacological strategies against obesity and the metabolic syndrome. Pharmacological Research, 2006, 53:482-491.
Li et al., Selective TBK1/IKKi dual inhibitors with anticancer potency, Int J Cancer, 2014, 134:1972-1980.
Li et al., Structure-based design, synthesis, and antimicrobial activity of indazole-derived SAH/MTA nucleosidase inhibitors. J Med Chem 2003, 46:5663-73.
Lindh et al., Multisite phosphorylation of adipocyte and hepatocyte phosphodiesterase 3B. Biochimica et Biophysica Acta, 2007, 1773:584-592.
Lipinski et al., Experimental and computational approaches to estimate solubility and permeability in drug discovery and development settings. Adv Drug Deliv Rev 2001, 46:3-26.
Lumeng et al., Macrophages block insulin action in adipocytes by altering expression of signaling and glucose transport proteins. American Journal of Physiology Endocrinology and Metabolism, 2007, 292:E166-E174.
Macarron et al., Impact of high-throughput screening in biomedical research. Nat Rev Drug Discov 2011, 10: 188-95.
Martins et al., Synthesis of substituted benzoxacycles via a domino ortho-alkylation/Heck coupling sequence. J Org Chem 2006, 71:4937-42.
MeSH Descriptor Data for Isoproterenol, accessed Jul. 5, 2016, 5 pages.
Misra et al., 1H-Pyrazolo[3,4-b]pyridine inhibitors of cyclin-dependent kinases. Bioorg Med Chem Lett 2003, 13:1133-6.
Miyamoto et al., Immunohistochemical analysis of Bcl-2, Bax, Bcl-X, and Mcl-1 expression in pancreatic cancers. Oncology. 1999;56(1):73-82.
Mowers et al., Inflammation produces catecholamine resistance in obesity via activation of PDE3B by the protein kinases Ikkε and TBK1, eLife, 2013, 2:e01119.
Muilenburg et al., Targeting Bcl-2-mediated cell death as a novel therapy in pancreatic cancer. J Surg Res., 2010, 163(2):276-81.
Neres et al., Non-nucleoside inhibitors of BasE, an adenylating enzyme in the siderophore biosynthetic pathway of the opportunistic pathogen *Acinetobacter baumannii*. J Med Chem 2013, 56, 2385-405.
Nikolovska-Coleska et al., Development and optimization of a binding assay for the XIAP BIR3 domain using fluorescence polarization. Anal Biochem 2004, 332:261-73.
Pal, et al., CCN6/WISP3 exerts its tumor suppressor function through regulation of BMP signaling by direct binding to BMP4 in the extracellular environment, 102nd AACR Annual Meeting 2011, Abstract No. 2200 for poster presentation, Abstract Only.
Nohara et al., Studies on antianaphylactic agents. 5. Synthesis of 3-(1H-tetrazol-5-yl)chromones, a new series of antiallergic substances. J Med Chem. Jan. 1977; 20(1):141-5.
Nohara et al., Studies on antianaphylactic agents. 7. Synthesis of antiallergic 5-oxo-5H-[1]benzopyrano[2,3-b]pyridines. J Med Chem. May 1985; 28(5):559-68.
Nohara et al., Studies on antianaphylactic agents—I : A facile synthesis of 4-oxo-4H-1-benzopyran-3-carboxaldehydes by Vilsmeier reagents. Tetrahedron 1974, vol. 30(19):3553-3561.
Obach, Mechanism of cytochrome P4503A4- and 2D6-catalyzed dehydrogenation of ezlopitant as probed with isotope effects using five deuterated analogs. Drug Metab Dispos. Dec. 2001;29(12):1599-607.
Oltersdorf et al., An inhibitor of Bcl-2 family proteins induces regression of solid tumours. Nature. Jun. 2, 2005;435(7042):677-81.
Ouchi et al., Adipokines in inflammation and metabolic disease. Nature Reviews Immunology, 2011, 11:85-97.
Palmer et al., Protein kinase A phosphorylation of human phosphodiesterase 3B promotes 14-3-3 protein binding and inhibits phosphatase-catalyzed inactivation, J Biol Chem, 2007, 282:9411-9419.
Park et al., Characterization of molecular recognition of STAT3 SH2 domain inhibitors through molecular simulation. J Mol Recognit. Mar.-Apr. 2011;24(2):254-65.
Parvatiyar et al., TAX1BP1 and A20 inhibit antiviral signaling by targeting TBK1-IKKi kinases, J Biol Chem, 2010, 285:14999-15009.
Petros et al., Discovery of a potent and selective Bcl-2 inhibitor using SAR by NMR. Bioorg Med Chem Lett. 2010, 20(22):6587-91.
Plomgaard et al., Tumor necrosis factor-alpha modulates human in vivo lipolysis, The Journal of Clinical Endocrinology and Metabolism, 2008, 93:543-549.
Pubchem Compound Summary for 6-(furan-2-yl)-3-methyl-1-pheylpyrazolo[3,4-b]pyridine-4-carboxylic acid. Https://pubchem.ncbi.nlm.hih.gov/compound/2998778#section=Top. Retrieved May 30, 2015, 13 pages.
Reilly et al., An inhibitor of the protein kinases TBK1 and IKK-epsilon improves obesity-related metabolic dysfunctions in mice. Nature Medicine, 2013, 19:313-321.
Reilly et al., A subcutaneous adipose tissue-liver signalling axis controls hepatic gluconeogenesis. Nat Commun. Jan. 12, 2015;6:6047.
Ren et al., Endocrine glands-derived vascular endothelial growth factor protects pancreatic cancer cells from apoptosis via upregulation of the myeloid cell leukemia-1. protein. Biochem Biophys Res Commun. Aug. 14, 2009;386(1):35-9.
Reynisdottir et al., Catecholamine resistance in fat cells of women with upper-body obesity due to decreased expression of beta 2-adrenoceptors. Diabetologia, 1994, 37:428-435.
Saltiel, Insulin resistance in the defense against obesity. Cell Metabolism, 2012, 15:798-804.
Schniewind et al., Resistance of pancreatic cancer to gemcitabine treatment is dependent on mitochondria-mediated apoptosis. Int J Cancer. Mar. 20, 2004;109(2):182-8.
Schrödinger Suite 2011 Induced Fit Docking protocol; Glide version 5.7, Schrödinger, LLC, New York, NY, 2009; Prime version 3.0, Schrödinger, LLC, New York, NY. 2011, 2 pages.
Schudt et al., Zardaverine as a selective inhibitor of phosphodiesterase isozymes, Biochemical Pharmacology, 1991, 42:153-162.
Sercel et al., Simple Synthesis of 4-Substituted 1(2H) Isoquinolinones via Electrophilic Trapping of Lithiated Mono and Dianion Precursors, Synthetic Communications: An International Journal for Rapid Communication of Synthetic Organic Chemistry, 37:23, 4199-4208 (2007).
Shoelson et al., Obesity, inflammation, and insulin resistance. Gastroenterology, 2007, 132:2169-2180.

(56) References Cited

OTHER PUBLICATIONS

Soares et al., Profiling the NIH Small Molecule Repository for compounds that generate H2O2 by redox cycling in reducing environments. Assay Drug Dev Technol. Apr. 2010;8(2):152-74.

Souza et al., TNF-alpha induction of lipolysis is mediated through activation of the extracellular signal related kinase pathway in 3T3-L1 adipocytes, Journal of Cellular Biochemistry, 2003, 89:1077-1086.

Stich et al., Hypocaloric diet reduces exercise-induced alpha 2-adrenergic antilipolytic effect and alpha 2-adrenergic receptor mRNA levels in adipose tissue of obese women, The Journal of Clinical Endocrinology and Metabolism, 2002, 87:1274-1281.

Testa, Prodrug research: futile or fertile? Biochem Pharmacol. Dec. 1, 2004;68(11):2097-106.

Tonn et al., Simultaneous analysis of diphenhydramine and a stable isotope analog (2H10)diphenhydramine using capillary gas chromatography with mass selective detection in biological fluids from chronically instrumented pregnant ewes. Biol Mass Spectrom. Nov. 1993;22(11):633-42.

Tsaioun et al., ADDME—Avoiding Drug Development Mistakes Early: central nervous system drug discovery perspective. BMC Neurol. Jun. 12, 2009;9 Suppl 1:S1.

Tse et al., ABT-263: a potent and orally bioavailable Bcl-2 family inhibitor. Cancer Res. May 1, 2008;68(9):3421-8.

Ukawa et al., Synthesis of the metabolites and degradation products of 2-amino-7-isopropyl-5-oxo-5H-[1]benzopyrano[2,3-b]pyridine-3-carboxylic acid (Amoxanox). Chem Pharm Bull (Tokyo). Oct. 1985; 33(10):4432-7.

Van Delft et al., The BH3 mimetic ABT-737 targets selective Bcl-2 proteins and efficiently induces apoptosis via Bak/Bax if Mcl-1 is neutralized. Cancer Cell. 2006;10:389-99.

Venkatesh et al., Role of the development scientist in compound lead selection and optimization. J Pharm Sci. Feb. 2000;89(2):145-54.

Volochnyuk et al., Approach to the library of fused pyridine-4-carboxylic acids by Combes-type reaction of acyl pyruvates and electron-rich amino heterocycles. J Comb Chem 2010, 12, 510-7.

Waibel et al., Bibenzyl- and stilbene-core compounds with non-polar linker atom substituents as selective ligands for estrogen receptor beta. Eur J Med Chem. Sep. 2009; 44(9):3412-24.

Wolen, The application of stable isotopes to studies of drug bioavailability and bioequivalence. J Clin Pharmacol. Jul.-Aug. 1986;26(6):419-24.

Wei et al., Inducing apoptosis and enhancing chemosensitivity to gemcitabine via RNA interference targeting Mcl-1 gene in pancreatic carcinoma cell. Cancer Chemother Pharmacol. Nov. 2008;62(6):1055-64.

Wellen et al., Inflammation, stress, and diabetes, The Journal of Clinical Investigation, 2005, 115:1111-1119.

Werner et al., Disruptive Yeast Tri-Hybrid Identifies Inducible IKK (IKKi) as a New Insulin Resistance Kinase. Abstract No. 158-OR, 64th Scientific Sessions, 2004, American Diabetes Association, 1 page.

Wertz et al., Sensitivity to antitubulin chemotherapeutics is regulated by MCL1 and FBW7. Nature. 2011, 471(7336):110-4.

Wunderlich et al., Hepatic NF-kappa B essential modulator deficiency prevents obesity-induced insulin resistance but synergizes with high-fat feeding in tumorigenesis, PNAS, 2008, 105:1297-1302.

Xu et al., Chemical probes that competitively and selectively inhibit Stat3 activation. PLoS One. 2009;4(3):e4783.

Ye et al., Regulation of energy metabolism by inflammation: a feedback response in obesity and calorie restriction. Aging, 2010, 2:361-368.

Yuan et al., Reversal of obesity- and diet-induced insulin resistance with salicylates or targeted disruption of Ikkbeta. Science, 2001, 293:1673-1677.

Zhang et al., Tumor necrosis factor-alpha stimulates lipolysis in differentiated human adipocytes through activation of extracellular signal-related kinase and elevation of intracellular cAMP. Diabetes, 2002, 51:2929-2935.

Zhou et al., Mcl-1, a Bcl-2 family member, delays the death of hematopoietic cells under a variety of apoptosis-inducing conditions. Blood. Jan. 15, 1997;89(2):630-43.

Zmuda-Trzebiatowska et al., Role of PDE3B in insulin-induced glucose uptake, GLUT-4 translocation and lipogenesis in primary rat adipocytes, 2006, Cell Signal 18:382-390.

European Search Report of related EP 14791582.1, dated Sep. 8, 2016, 7 pages.

International Search Report and Written Opinion for PCT/US2012/059216, dated Mar. 25, 2013,12 pages.

International Search Report and Written Opinion for PCT/US2012/068570, dated Feb. 28, 2013, 9 pages.

International Search Report and Written Opinion for PCT/US2014/015387, dated May 14, 2014, 9 pages.

International Search Report and Written Opinion, International Application No. PCT/US2015/024231, dated Oct. 1, 2015, 10 pages.

International Search Report and Written Opinion for PCT/US2017/015391, dated Apr. 7, 2017, 6 pages.

Kang et al., Randomized controlled trial to investigate the effects of a newly developed formulation of phentermine diffuse-controlled release for obesity. Diabetes Obes Metab. Oct. 2010;12(10):876-82.

European Search Report of related EP 14881460.1, dated Aug. 18, 2017, 10 pages.

\* cited by examiner

Figure 1
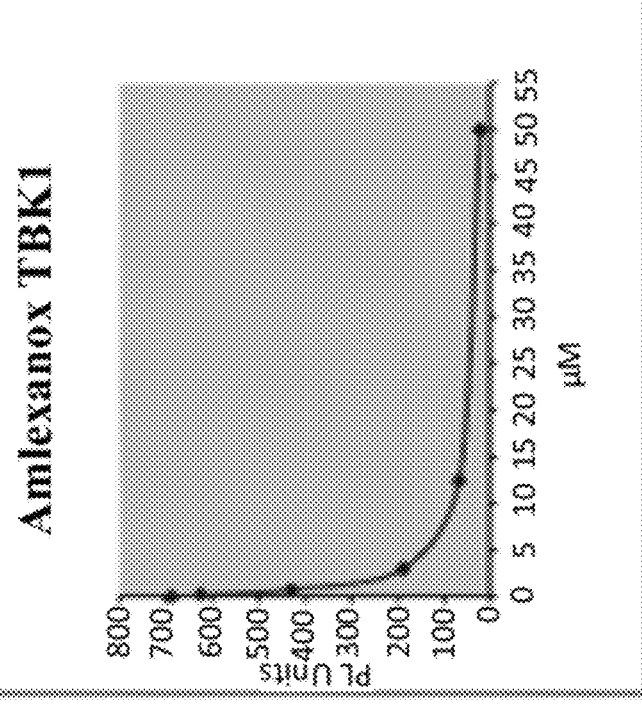
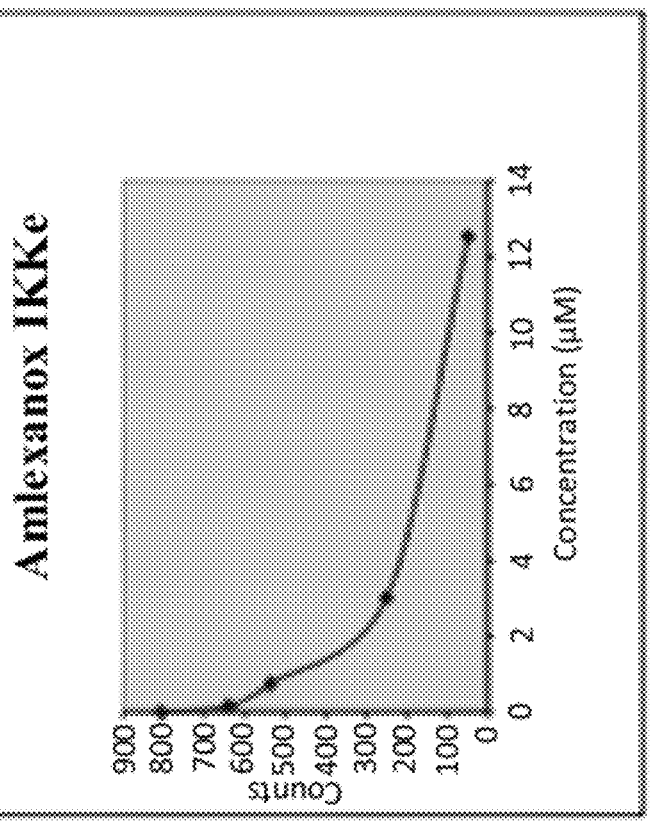

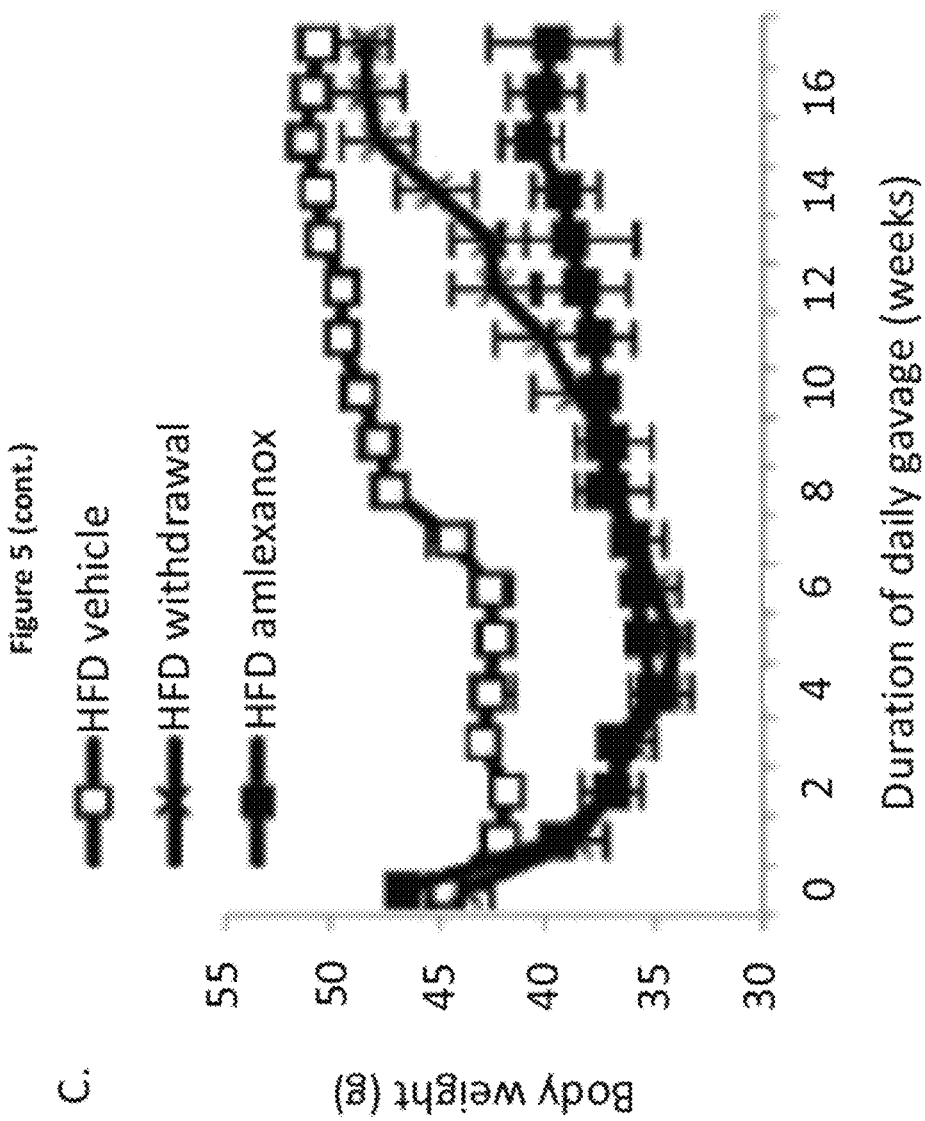

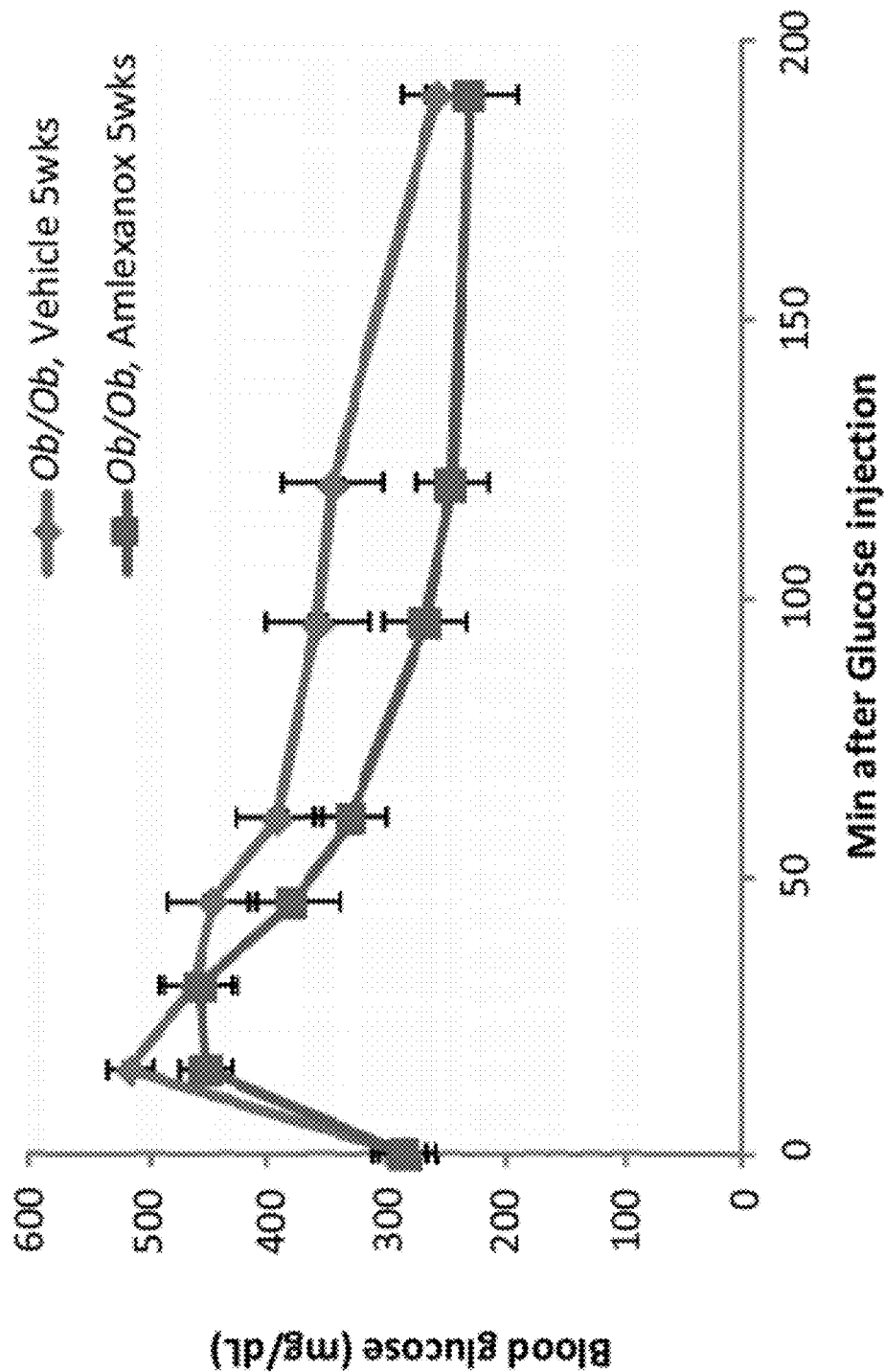

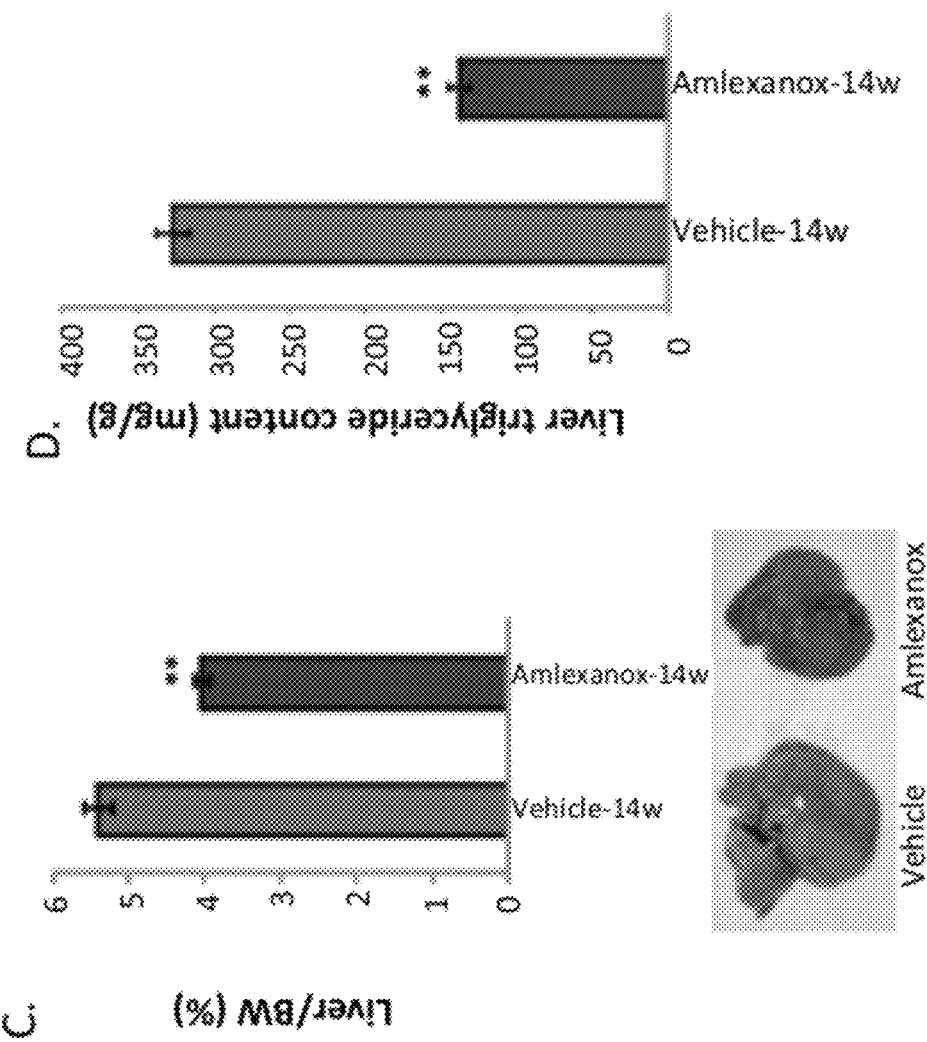

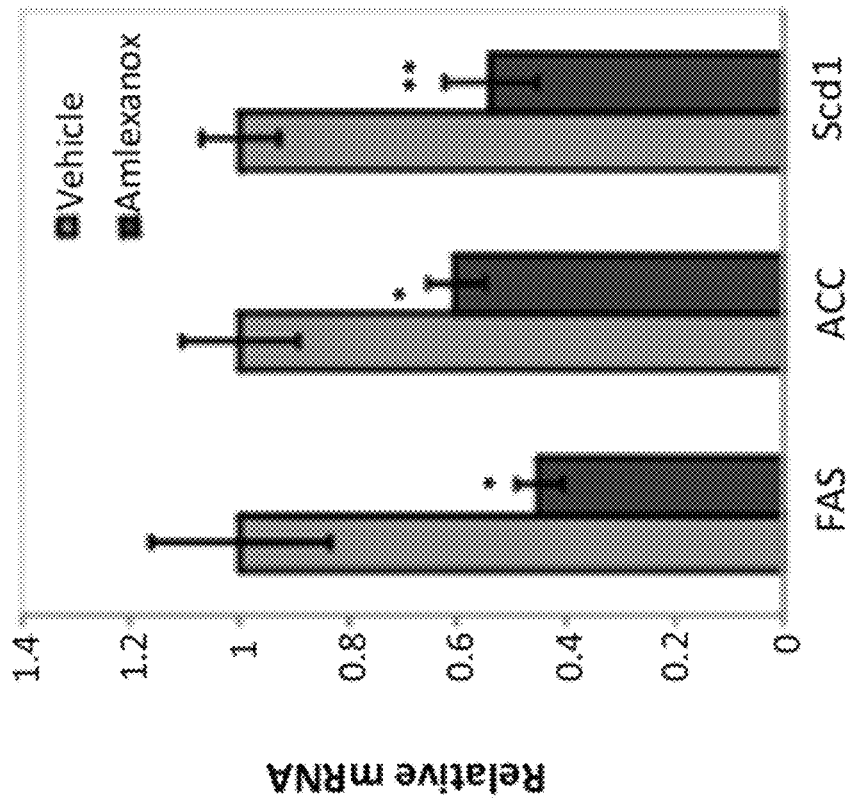

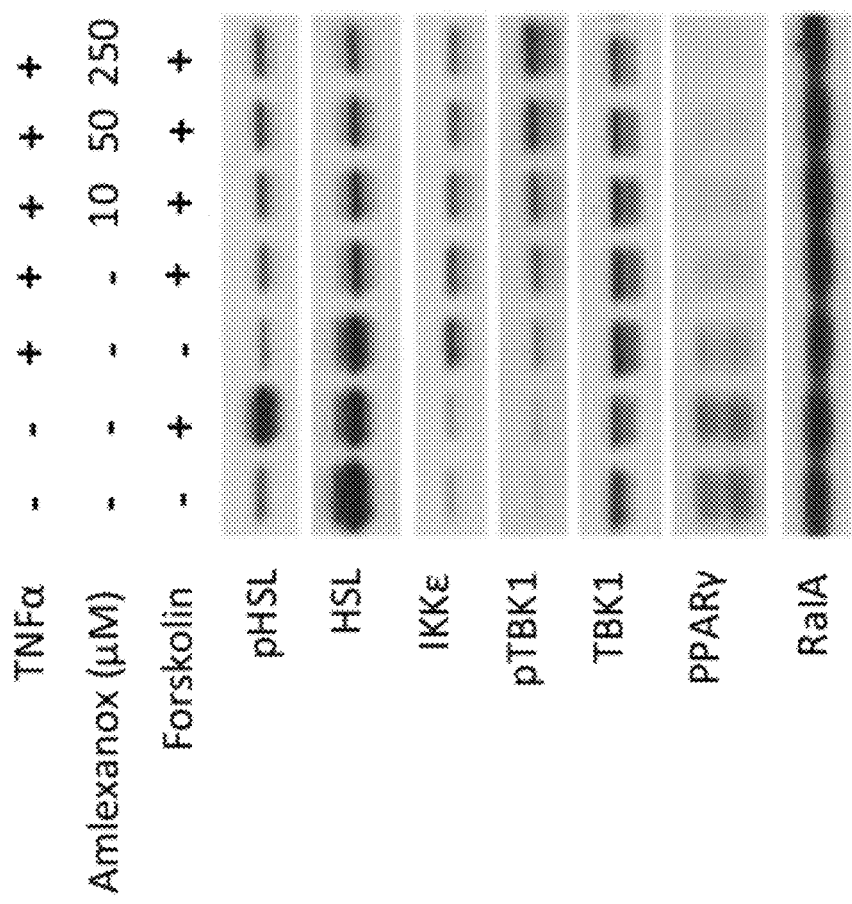

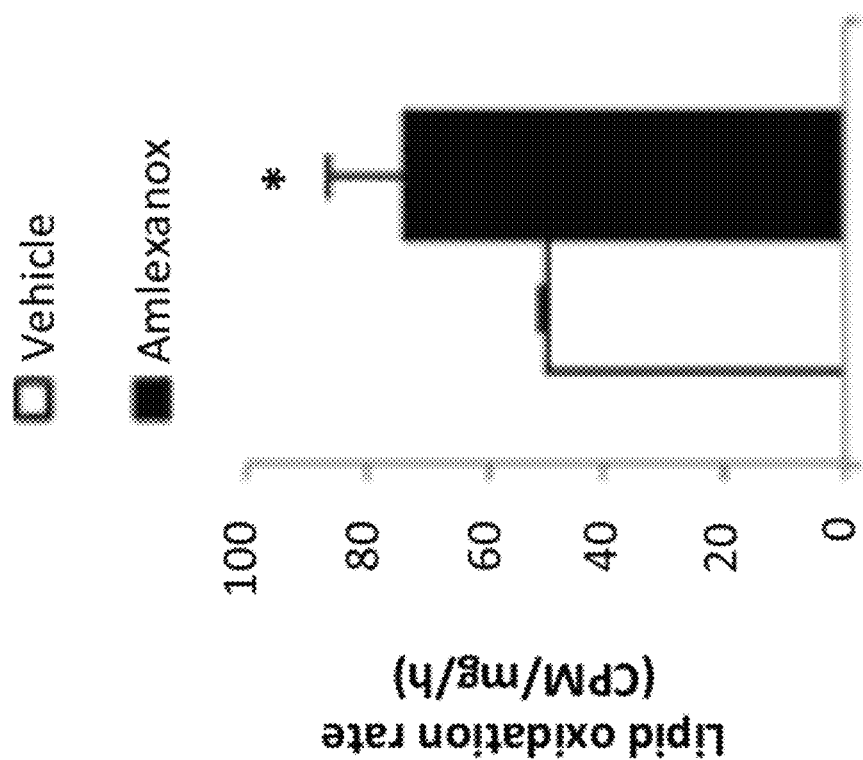

COMPOSITIONS AND METHODS FOR THE TREATMENT OF OBESITY AND RELATED DISORDERS

This application claims priority to U.S. Provisional Application 61/442,558, filed Feb. 14, 2011, which is herein incorporated by reference in its entirety for all purposes.

FIELD

Provided herein are compositions and methods for the treatment of obesity and related disorders, including, but not limited to insulin resistance, diabetes, steatosis, nonalcoholic steatotic hepatitis, and atherosclerosis. For example, in some embodiments, compositions and methods are provided employing amlexanox, a derivative thereof or a pharmaceutically acceptable salt thereof, alone or in combination with other agents and/or medical interventions, for the treatment, prevention, and management of such diseases and conditions.

BACKGROUND

Generally, obesity is defined as an excess of adipose tissue. Clinically, it is generally defined as that amount of adiposity that imparts a health risk. Even mild obesity, at 20% over desirable weight according to standard height-weight charts, may increase the risk for disease and premature death. While the etiology of obesity and diabetes is not entirely overlapping, it is now amply clear that both share appreciable biochemical and physiological components.

The incidence of the metabolic disorders of diabetes and obesity has reached epidemic levels. It has been estimated that over 120 million Americans are clinically over-weight and over 25 million have diabetes, including 1.9 million new cases in 2010 among those aged 20 and older. Obesity and diabetes can cause or contribute to the development of, or at least affect the treatment of, other diseases and disorders such as cardiovascular diseases, stroke, hypertension, kidney failure, asthma, and cancer. The economic burden of diabetes alone was estimated to be over $174 billion per year in 2007. Obesity and diabetes have a major impact on human health and the various national healthcare systems all over the world.

Recently launched weight-loss drugs have failed or have demonstrated limited efficacy and undesirable side effects. Similarly, despite a tremendous medical need, the pharmaceutical industry has realized only limited success developing therapeutics to manage diabetes. The most common therapeutics (sulfonylureas) are not effective and the most promising new drugs (thiazolidinediones) have demonstrated rare but fatal side effects. Thus, there is an urgent need for a more comprehensive understanding of the molecular basis of obesity and diabetes, for tests that allow early detection of predispositions to the disorders, and for more effective pharmaceuticals for preventing and treating the diseases and conditions.

SUMMARY

Provided herein are compositions and methods for the treatment of obesity, insulin resistance, diabetes, and steatosis. For example, in some embodiments, pharmaceutically acceptable compositions and methods are provided employing amlexanox, a derivative thereof, or a pharmaceutically acceptable salt thereof, alone or in combination with other agents and/or medical interventions, for the treatment, prevention, and management of such diseases and conditions.

In some embodiments, provided herein are methods of treatment comprising: administering a pharmaceutically effective amount of amlexanox, a derivative thereof, or a pharmaceutically acceptable salt thereof, alone or in combination with another agent, to a subject with a condition associated with obesity or insulin resistance. In some embodiments, the administration causes one or more of: a reduction in or elimination of one or more symptoms of the condition, prevention of increased severity of one or more symptoms of the condition, and/or reduction, prevention, or elimination of further diseases or conditions.

In certain embodiments, the insulin resistance is in the subject's adipocyte cells, liver cells, or muscle cells. In particular embodiments, the insulin resistance causes the subject to have impaired glucose metabolism. In further embodiments, the administering causes an increase in glucose metabolism by adipocytes and correction in the appearance of adipose tissue macrophages of the subject. In some embodiments, the increase in glucose metabolism is caused by increased insulin receptor signaling in response to insulin.

In particular embodiments, the administering causes a reduction of body fat in the subject (e.g., the size of adipocytes in the subject is reduced). In certain embodiments, the administering causes the patient to lose at least 10 pounds (e.g., 10, 15, 20, 35, 60, 100, 200 or more pounds). In some embodiments, the administration causes at least a 5% reduction in the patient's body weight (e.g., at least 7%, 10%, 20%, 30%, 50%, 75% reduction or more).

In some embodiments, the condition treated is obesity. In other embodiments, the condition treated is diabetes (e.g., type II or both types I and II). In further embodiments, the condition treated is insulin resistance.

In some embodiments, the subject is experiencing or is at risk of experiencing a condition such as obesity, diabetes, and insulin resistance. In some embodiments, the treatment results in an outcome of increased glucose metabolism, reduction in body fat, lack of increase in body fat, increased insulin receptor signaling, reduction in or prevention of chronic inflammation in the liver, reduction in or prevention of chronic inflammation in adipose tissue, reduction in or prevention of hepatic steatosis, promotion of metabolic energy expenditure, reduction in circulating free fatty acids, and/or reduction in cholesterol.

Conditions and disease states that may be treated by the methods and pharmaceutically acceptable compositions provided herein include, but are not limited to: diabetes mellitus, type II diabetes, metabolic syndrome, insulin resistance syndrome, lipid metabolic conditions, and hepatic steatosis disease (also referred to as fatty liver disease). Fatty liver disease can range from fatty liver alone (steatosis) to fatty liver associated with inflammation (steatohepatitis). This condition can occur with alcohol use (alcohol-related fatty liver) or in the absence of alcohol use (nonalcoholic fatty liver disease (NAFLD)). Other factors that may lead to fatty liver disease include, but are not limited to, drugs (e.g., amiodarone, tamoxifen, methotrexate), alcohol, metabolic abnormalities (e.g., galactosemia, glycogen storage diseases, homocystinuria, tyrosinemia), nutritional status (e.g., overnutrition, severe malnutrition, total parenteral nutrition (TPN), starvation diet), or other health problems (e.g., celiac sprue, Wilson disease). Individuals genetically predisposed to fatty liver disease may exhibit normal or underweight body composition.

The compositions and methods provided herein find use in the treatment of overweight subjects and/or prevention of obesity. The World Health Organization (WHO) provides the most widely accepted clinical definition of obesity. Under this convention for adults, grade 1 overweight (commonly and simply called overweight) is a body mass index (BMI) of 25-29.9 kg/m$^2$. Grade 2 overweight (commonly called obesity) is a BMI of 30-39.9 kg/m$^2$. Grade 3 overweight (commonly called severe or morbid obesity) is a BMI greater than or equal to 40 kg/m$^2$. The surgical literature often uses a different classification to recognize particularly severe obesity. In this setting, a BMI greater than 40 kg/m$^2$ is described as severe obesity, a BMI of 40-50 kg/m$^2$ is termed morbid obesity, and a BMI greater than 50 kg/m$^2$ is termed super obese. The definition of obesity in children involves BMIs greater than the 85th (commonly used to define overweight) or the 95th (commonly used to define obesity) percentile, respectively, for age-matched and sex-matched control subjects. Secondary causes of obesity include but are not limited to hypothyroidism, Cushing syndrome, insulinoma, hypothalamic obesity, polycystic ovarian syndrome, genetic syndromes (e.g., Prader-Willi syndrome, Alström syndrome, Bardet-Biedl syndrome, Cohen syndrome, Böjeson-Forssman-Lehmann syndrome, Fröhlich syndrome), growth hormone deficiency, oral contraceptive use, medication-induced obesity (e.g., phenothiazines, sodium valproate, carbamazepine, tricyclic antidepressants, lithium, glucocorticoids, megestrol acetate, thiazolidine diones, sulphonylureas, insulin, adrenergic antagonists, serotonin antagonists (especially cyproheptadine)), eating disorders (especially binge-eating disorder, bulimia nervosa, night-eating disorder), hypogonadism, pseudohypoparathyroidism, and obesity related to tube feeding.

In some embodiments, the methods and pharmaceutically acceptable compositions of amlexanox or a derivative thereof provided herein are used to treat a subject having a condition associated with obesity, insulin resistance, or hepatic steatosis, wherein the subject does not have an allergy, an apthous ulcer, or bronchial asthma. In some embodiments, the methods and pharmaceutically acceptable compositions of amlexanox or a derivative thereof provided herein are used to treat a subject having a condition associated with obesity, insulin resistance, hepatic steatosis, or one or more of the above diseases or conditions but are not used to treat one or more of the following diseases or conditions or are lacking at least one (or multiple or all) of the following diseases or conditions or are not in need of treatment of at least one (or multiple or all) of the following diseases or conditions: allergies, hay fever, asthma (e.g., bronchial asthma), aphthous ulcers, rhinitis, bronchitis, lung inflammation, osteoarthritis, juvenile arthritis, rheumatoid arthritis, spondylo arthopathies, gouty arthritis, chronic granulomatous diseases such as tuberculosis, leprosy, sarcoidosis, and silicosis, nephritis, amyloidosis, ankylosing spondylitis, chronic bronchitis, scleroderma, systemic lupus erythematosus, polymyositis, appendicitis, inflammatory bowel disease, Crohn's disease, gastritis, irritable bowel syndrome, ulcerative colitis, colorectal cancer, Sjorgen's syndrome, Reiter's syndrome, psoriasis, pelvic inflammatory disease, orbital inflammatory disease, thrombotic disease, menstrual cramps, tendinitis, bursitis, psoriasis, eczema, burns, dermatitis, and inappropriate allergic responses to environmental stimuli such as poison ivy, pollen, insect stings, and certain foods, including atopic dermatitis and contact dermatitis, migraine headaches, periarteritis nodosa, thyroiditis, aplastic anemia, Hodgkin's disease, sclerodoma, rheumatic fever, myasthenia gravis, sarcoidosis, nephrotic syndrome, Behcet's syndrome, polymyositis, gingivitis, hypersensitivity, conjunctivitis, swelling occurring after injury, lipopolysaccharide-induced septic shock, tissue regeneration, neurodegenerative disease (e.g., Alzheimer's disease), tissue rejection, osteoporosis, cachexia, and neurodegeneration. In some embodiments, the methods and compositions are used to treat subjects not in need of tissue regeneration. In some embodiments, the methods and compositions are used to treat subjects lacking cell proliferative disorders such as, for instance, benign prostate hyperplasia, familial adenomatosis, polyposis, neuro-fibromatosis, psoriasis, pulmonary fibrosis, and arthritis glomerulonephritis.

In some embodiments, the methods and pharmaceutically acceptable compositions provided herein are not used to treat one or more of the following cancers or are used to treat subjects who do not have at least one of the following cancers: carcinoma such as bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage, including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myclogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

In some embodiments, the methods provided comprise testing a subject for a disease or condition such as impaired insulin signaling, obesity, diabetes, insulin resistance, metabolic syndrome, hepatic steatosis, chronic inflammation in liver, and chronic inflammation in adipose tissue, followed by administering amlexanox, a derivative thereof, or a pharmaceutically acceptable salt thereof, alone or in combination with other agents. In some embodiments, methods comprise administering to a subject amlexanox, a derivative thereof, or a pharmaceutically acceptable salt thereof, alone or in combination with other agents, followed by testing the subject for a disease or a condition such as impaired insulin signaling, obesity, diabetes, insulin resistance, metabolic syndrome, hepatic steatosis, chronic inflammation in liver, and chronic inflammation in adipose tissue. In some embodiments, methods comprise testing a subject for a disease or condition such as impaired insulin signaling, obesity, diabetes, insulin resistance, metabolic syndrome, hepatic steatosis, chronic inflammation in liver, and chronic inflammation in adipose tissue, followed by administering amlexanox, a derivative thereof, or a pharmaceutically acceptable salt thereof, alone or in combination with other agents, followed by a second round of testing for a disease or condition such as impaired insulin signaling, obesity, diabetes, insulin resistance, metabolic syndrome, hepatic steatosis, chronic inflammation in liver, and chronic inflammation in adipose tissue (e.g., to monitor the effect of the treatment). In some embodiments, methods comprise testing a subject for a disease or condition such as impaired insulin signaling, obesity, diabetes, insulin resistance, metabolic syndrome, hepatic steatosis, chronic inflammation in liver, and chronic inflammation in adipose tissue, followed by administering amlexanox, a derivative thereof, or a pharmaceutically acceptable salt thereof, alone or in combination with other agents, followed by a second round of testing for a disease or condition such as impaired insulin signaling, obesity, diabetes, insulin resistance, metabolic syndrome, hepatic steatosis, chronic inflammation in liver, and chronic inflammation in adipose tissue, and a second administration of amlexanox, a derivative thereof, or a pharmaceutically acceptable salt thereof, alone or in combination with other agents, with this second administration being modified in dose, duration, frequency, or administration route in a manner dependent upon the results of the prior testing.

In some embodiments, the technology provided comprises use of amlexanox, a derivative thereof, or a pharmaceutically acceptable salt thereof, alone or in combination with other agents in the manufacture of a medicament for the treatment of a condition such as impaired insulin signaling, obesity, diabetes, insulin resistance, metabolic syndrome, hepatic steatosis, chronic inflammation in liver, and chronic inflammation in adipose tissue.

In some embodiments, the technology provides amlexanox, a derivative thereof, or a pharmaceutically acceptable salt thereof, for the treatment of a condition associated with obesity, insulin resistance, or hepatic steatosis.

In some embodiments, amlexanox, a derivative thereof, or a pharmaceutically acceptable salt thereof, is co-administered with one or more additional therapeutic agents or medical interventions. In some embodiments, co-administration involves co-formulation of two or more agents together into the same medicament. In other embodiments, the agents are in separate formulations but are administered together, either simultaneously or in sequence (e.g., separated by one or more minutes, hours, days, etc.). In some embodiments, where a synergistic or additive benefit is achieved, the co-administered agent may be provided at a lower dose than would normally be administered if that agent were being used in isolation to treat the disease or condition. For example, in some embodiments, one or more of the following agents or interventions is co-administered or co-applied with amlexanox, a derivative thereof, or a pharmaceutically acceptable salt thereof: low calorie diet, very low calorie diet (less than 800 calories per day), low-fat diet, gluten-free diet, exercise, appetite-suppressant medications.

BRIEF DESCRIPTION OF THE DRAWINGS

These and other features, aspects, and advantages of the present technology will become better understood with regard to the following drawings:

FIG. 1A shows a plot of IKKe phosphorylation activity measured in vitro as a function of amlexanox concentration.

FIG. 1B shows a plot of TBK1 phosphorylation activity as a function of amlexanox concentration.

FIG. 10 shows relative gene expression (as relative mRNA levels) for lipogenic genes expressed in livers of amlexanox-treated Ob/ob mice.

FIG. 24 is a plot showing the lipid oxidation rate in ex vivo BAT treated with amlexanox (black bar) or vehicle control (white bar). (n=6 per group). *P value<0.05 vehicle versus amlexanox treated.

DETAILED DESCRIPTION

Figure 2:
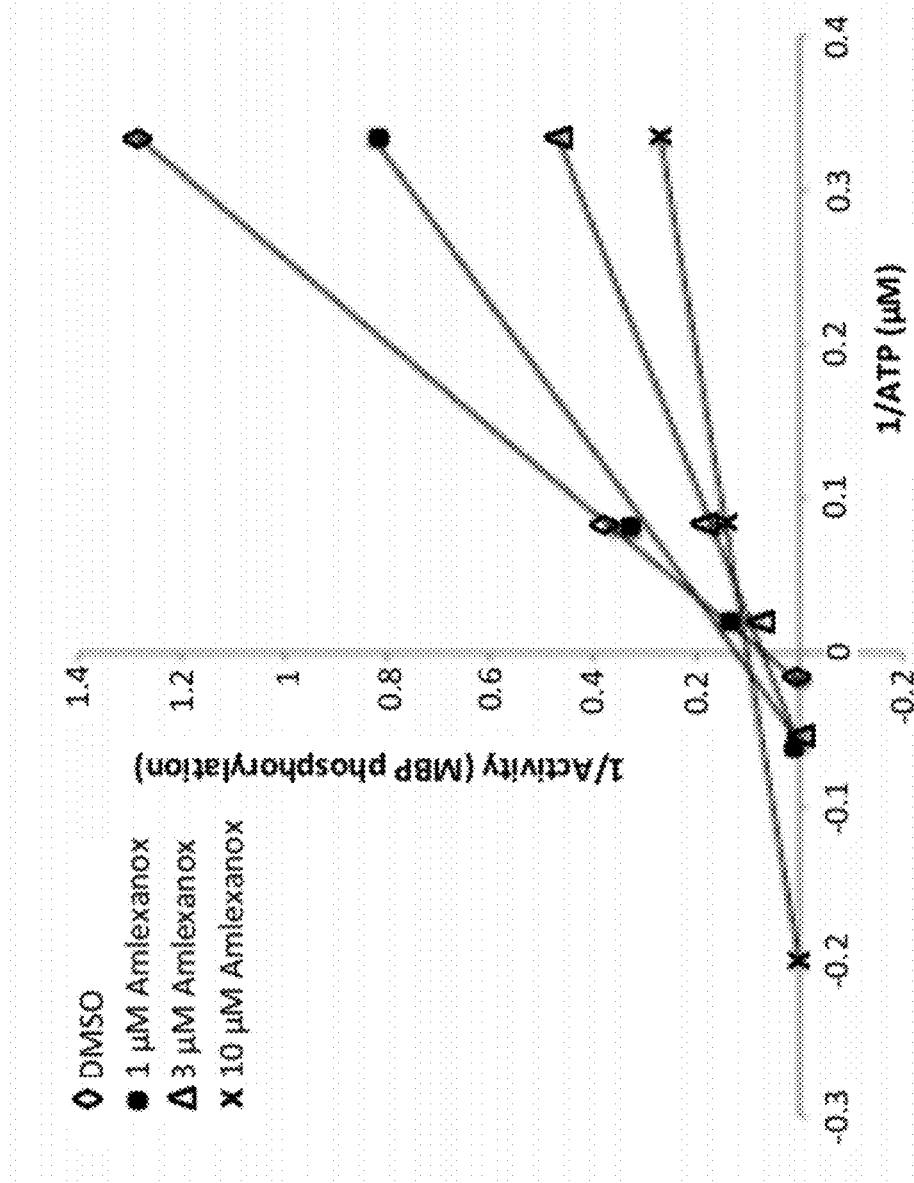
FIG. 2 shows a double-reciprocal plot depicting competitive inhibition of ATP binding to IKKe by amlexanox.

Provided herein are compositions and methods for the treatment of obesity, insulin resistance, or hepatic steatosis. For example, in some embodiments, compositions and methods are provided employing amlexanox, a derivative thereof, or a pharmaceutically acceptable salt thereof, alone or in combination with other agents and/or medical interventions, for the treatment, prevention, and management of such diseases and conditions.

Definitions

To facilitate an understanding of embodiments described herein, a number of terms are defined below.

As used herein, "a" or "an" or "the" can mean one or more than one. For example, "a" cell can mean one cell or a plurality of cells.

As used herein, "active" or "activity" refers to native or naturally occurring biological and/or immunological activity.

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the terms "subject" and "patient" refer to any animal, such as a mammal like a dog, cat, bird, livestock, and preferably a human (e.g., a human with a disease such as obesity, diabetes, or insulin resistance).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive versus conventional treatment).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present technology.

As used herein, the terms "alkyl" and the prefix "alk-" are inclusive of both straight chain and branched chain saturated or unsaturated groups, and of cyclic groups, e.g., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms. Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulihydryl, alkylthio, arylthio, halogen, alkylsilyl, hydroxyl, fluoroalkyl, perfluoroalkyl, amino, aminoalkyl, disubstituted amino, quaternary amino, hydroxyalkyl, carboxyalkyl, and carboxyl groups. When the prefix "alk" is used, the number of carbons contained in the alkyl chain is given by the range that directly precedes this term, with the number of carbons contained in the remainder of the group that includes this prefix defined elsewhere herein. For example, the term "$C_1$-$C_4$ alkaryl" exemplifies an aryl group of from 6 to 18 carbons (e.g., see below) attached to an alkyl group of from 1 to 4 carbons.

As used herein, the term "aryl" refers to a carbocyclic aromatic ring or ring system. Unless otherwise specified, aryl groups are from 6 to 18 carbons. Examples of aryl groups include phenyl, naphthyl, biphenyl, fluorenyl, and indenyl groups.

As used herein, the term "heteroaryl" refers to an aromatic ring or ring system that contains at least one ring heteroatom (e.g., O, S, Se, N, or P). Unless otherwise specified, heteroaryl groups are from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl groups.

As used herein, the term "heterocycle" refers to a non-aromatic ring or ring system that contains at least one ring heteroatom (e.g., O, S, Se, N, or P). Unless otherwise specified, heterocyclic groups are from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents selected from the group consisting of $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, alkaryl (where the alkyl group has from 1 to 4 carbon atoms), and alkheteroaryl (where the alkyl group has from 1 to 4 carbon atoms).

As used herein, the term "alkoxy" refers to a chemical substituent of the formula —OR, where R is an alkyl group. By "aryloxy" is meant a chemical substituent of the formula —OR', where R' is an aryl group.

As used herein, the term "$C_{x-y}$ alkaryl" refers to a chemical substituent of formula —RR', where R is an alkyl group of x to y carbons and R' is an aryl group as defined elsewhere herein.

As used herein, the term "$C_{x-y}$ alkheteraryl" refers to a chemical substituent of formula RR", where R is an alkyl group of x to y carbons and R" is a heteroaryl group as defined elsewhere herein.

As used herein, the term "halide" or "halogen" or "halo" refers to bromine, chlorine, iodine, or fluorine.

As used herein, the term "non-vicinal O, S, or N" refers to an oxygen, sulfur, or nitrogen heteroatom substituent in a linkage, where the heteroatom substituent does not form a bond to a saturated carbon that is bonded to another heteroatom.

For structural representations where the chirality of a carbon has been left unspecified it is to be presumed by one skilled in the art that either chiral form of that stereocenter is possible.

Embodiments of the Technology

In some embodiments, the compositions and methods employ amlexanox (2-amino-7-isopropyl-1-azaxanthone-3-carboxylic acid; 2-amino-7-isopropyl-5-oxo-5H-chromeno[2,3-b]pyridine-3-carboxylic acid), a derivative thereof, or a pharmaceutically acceptable salt thereof. Amlexanox and its synthesis are described in U.S. Pat. No. 4,143,042, herein incorporated by reference in its entirety.

In some embodiments, the compound has the structure of Formula I:

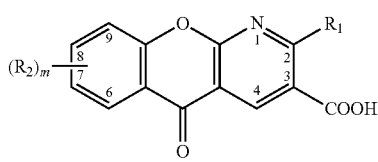

wherein $R_1$ is a hydrogen, alkyl, phenyl, carboxyl, hydroxyl, alkoxy, or amino group, which may be unsubstituted or substituted by one alkyl; m is 0, 1 or 2; and $R_2$ is alkyl, alkoxy, halogen, nitro, hydroxy, carboxyl, butadienylene (—CH=CH—CH=CH—), which forms a benzene ring with any adjacent carbon atoms or amino group, which may be unsubstituted or substituted by at least one alkyl, and their physiologically acceptable salts. The substituents designated in each of the above-mentioned formulae may be substituted at optional position or positions of the 6-, 7-, 8-, or 9-positions of the azaxanthone ring.

In Formula (I), the alkyl group represented by $R_1$ and $R_2$ may be any of straight-chain, branched, or cyclic alkyl group having 1 to 6 carbon atoms. Typical examples of the alkyl group may be methyl, ethyl, propyl, isopropyl, butyl, isobutyl, sec-butyl, tert-butyl, pentyl, cyclopentyl, hexyl, cyclohexyl, etc.

The alkoxy group represented by $R_1$ and $R_2$ may, for example, be that having 1 to 4 carbon atoms in the alkyl moieties, such as methoxy, ethoxy, propoxy, isopropoxy, butoxy, etc.

The mono-alkyl substituted amino group represented by $R_1$ may be that having 1 to 3 carbon atoms in the alkyl moieties, such as methylamino, ethylamino, propylamino, or isopropylamino. The halogen represented by $R_2$ may be chlorine, bromine, iodine, or fluorine.

The alkyl substituted amino group represented by $R_2$ includes mono- or di-alkyl substituted ones whose alkyl moiety is that having 1 to 3 carbon atoms, e.g., methylamino, ethylamino, propylamino, isopropylamino, dimethylamino, diethylamino, or dipropylamino.

The compound of general Formula (I) can be converted to the corresponding organic amine salts, alkali metal salts, or ammonium salts by reacting (I) in the per se conventional manner with an organic amine (e.g., ethanolamine, diethanolamine, dl-methylephedrin, 1-(3,5-dihydroxyphenyl)-L-isopropylaminoethanol, isoproterenol, dextromethorphan, hetrazan(diethylcarbamazine), diethylamine, triethylamine, etc.), an alkali metal hydroxide (e.g., sodium hydroxide, potassium hydroxide, etc.) or ammonia, for example by mixing them together and heating in a suitable solvent.

It is generally contemplated that the compounds according to the technology provided are formulated for administration to a mammal, and especially to a human with a condition that is responsive to the administration of such compounds. Therefore, where contemplated compounds are administered in a pharmacological composition, it is contemplated that the contemplated compounds are formulated in admixture with a pharmaceutically acceptable carrier. For example, contemplated compounds can be administered orally as pharmacologically acceptable salts, or intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

In certain pharmaceutical dosage forms, prodrug forms of contemplated compounds may be formed for various purposes, including reduction of toxicity, increasing the organ or target cell specificity, etc. Among various prodrug forms, acylated (acetylated or other) derivatives, pyridine esters, and various salt forms of the present compounds are preferred. One of ordinary skill in the art will recognize how to readily modify the present compounds to prodrug forms to facilitate delivery of active compounds to a target site within the host organism or patient. One of ordinary skill in the art will also take advantage of favorable pharmacokinetic parameters of the prodrug forms, where applicable, in delivering the present compounds to a targeted site within the host organism or patient to maximize the intended effect of the compound. Similarly, it should be appreciated that contemplated compounds may also be metabolized to their biologically active form, and all metabolites of the compounds herein are therefore specifically contemplated. In addition, contemplated compounds (and combinations thereof) may be administered in combination with yet further agents for treating obesity and related disorders, including, but not limited to insulin resistance, diabetes, steatosis, nonalcoholic steatotic hepatitis, and atherosclerosis.

With respect to administration to a subject, it is contemplated that the compounds be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication, and other factors that those skilled in the art will recognize.

In some embodiments, amlexanox, a derivative thereof, or a pharmaceutically acceptable salt thereof, is administered in a pharmaceutically effective amount. In some embodiments, amlexanox, a derivative thereof, or a pharmaceutically acceptable salt thereof, is administered in a therapeutically effective dose.

The dosage amount and frequency are selected to create an effective level of the compound without substantially harmful effects. When administered orally or intravenously, the dosage of amlexanox or related compounds will generally range from 0.001 to 10,000 mg/kg/day or dose (e.g., 0.01 to 1000 mg/kg/day or dose; 0.1 to 100 mg/kg/day or dose).

Methods of administering a pharmaceutically effective amount include, without limitation, administration in parenteral, oral, intraperitoneal, intranasal, topical, sublingual, rectal, and vaginal forms. Parenteral routes of administration include, for example, subcutaneous, intravenous, intramuscular, intrastemal injection, and infusion routes. In some embodiments, amlexanox, a derivative thereof, or a pharmaceutically acceptable salt thereof, is administered orally.

Pharmaceutical compositions preferably comprise one or more compounds of the present technology associated with one or more pharmaceutically acceptable carriers, diluents, or excipients. Pharmaceutically acceptable carriers are known in the art such as those described in, for example, *Remingtons Pharmaceutical Sciences,* Mack Publishing Co. (A. R. Gennaro edit. 1985), explicitly incorporated herein by reference for all purposes.

Accordingly, in some embodiments, the composition is formulated as a tablet, a capsule, a time release tablet, a time release capsule; a time release pellet; a slow release tablet, a slow release capsule; a slow release pellet; a fast release tablet, a fast release capsule; a fast release pellet; a sublingual tablet; a gel capsule; a microencapsulation; a transdermal delivery formulation; a transdermal gel; a transdermal patch; a sterile solution; a sterile solution prepared for use as an intramuscular or subcutaneous injection, for use as a direct injection into a targeted site, or for intravenous administration; a solution prepared for rectal administration; a solution prepared for administration through a gastric feeding tube or duodenal feeding tube; a suppository for rectal administration; a liquid for oral consumption prepared as a solution or an elixir; a topical cream; a gel; a lotion; a tincture; a syrup; an emulsion; or a suspension.

In some embodiments, the time release formulation is a sustained-release, sustained-action, extended-release, controlled-release, modified release, or continuous-release mechanism, e.g., the composition is formulated to dissolve quickly, slowly, or at any appropriate rate of release of amlexanox over time.

In some embodiments, the compositions are formulated so that the active ingredient is embedded in a matrix of an insoluble substance (e.g., various acrylics, chitin) such that the dissolving drug finds its way out through the holes in the matrix, e.g., by diffusion. In some embodiments, the formulation is enclosed in a polymer-based tablet with a laser-drilled hole on one side and a porous membrane on the other side. Stomach acids push through the porous membrane, thereby pushing the drug out through the laser-drilled hole. In time, the entire drug dose releases into the system while the polymer container remains intact, to be excreted later through normal digestion. In some sustainid-release formulations, the amlexanox dissolves into the matrix and the matrix physically swells to form a gel, allowing the drug to exit through the gel's outer surface. In some embodiments, the formulations are in a micro-encapsulated form, e.g., which is used in some embodiments to produce a complex dissolution profile. For example, by coating amlexanox around an inert core and layering it with insoluble substances to form a microsphere, some embodiments provide more consistent and replicable dissolution rates in a convenient format that is combined in particular embodiments with other controlled (e.g., instant) release pharmaceutical ingredients, e.g., to provide a multipart gel capsule.

In some embodiments, the pharmaceutical preparations and/or formulations of the technology are provided in particles. Particles as used herein means nano or microparticles (or in some instances larger) that can consist in whole or in part of amlexanox or the other therapeutic agent(s) as described herein. The particles may contain the preparations and/or formulations in a core surrounded by a coating, including, but not limited to, an enteric coating. The preparations and/or formulations also may be dispersed throughout the particles. The preparations and/or formulations also may be adsorbed into the particles. The particles may be of any order release kinetics, including zero order release, first order release, second order release, delayed release, sustained release, immediate release, and any combination thereof, etc. The particle may include, in addition to the t preparations and/or formulations, any of those materials routinely used in the art of pharmacy and medicine, including, but not limited to, erodible, nonerodible, biodegradable, or nonbiodegradable material or combinations thereof. The particles may be microcapsules which contain the formulation in a solution or in a semi-solid state. The particles may be of virtually any shape.

Both non-biodegradable and biodegradable polymeric materials can be used in the manufacture of particles for delivering the preparations and/or formulations. Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules,* (1993) 26: 581-587, the teachings of which are incorporated herein by reference. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenylmethacrylate), poly(methyl acrylate), poly(isopropyl acrylate), poly(isobutyl acrylate), and poly(octadecyl acrylate).

The technology also provides methods for preparing stable pharmaceutical preparations containing aqueous solutions of amlexanox or salts thereof to inhibit formation of amlexanox degradation products. A solution is provided that contains amlexanox or salts thereof and at least one amlexanox inhibiting agent. The solution is processed under at least one sterilization technique prior to and/or after terminal filling the solution in the sealable container to form a stable pharmaceutical preparation. The present formulations may be prepared by various methods known in the art so long as the formulation is substantially homogenous, e.g., the pharmaceutical is distributed substantially uniformly within the formulation. Such uniform distribution facilitates control over drug release from the formulation.

In some embodiments, the amlexanox is formulated with a buffering agent. The buffering agent may be any pharmaceutically acceptable buffering agent. Buffer systems include citrate buffers, acetate buffers, borate buffers, and phosphate buffers. Examples of buffers include citric acid, sodium citrate, sodium acetate, acetic acid, sodium phosphate and phosphoric acid, sodium ascorbate, tartartic acid, maleic acid, glycine, sodium lactate, lactic acid, ascorbic acid, imidazole, sodium bicarbonate and carbonic acid, sodium succinate and succinic acid, histidine, and sodium benzoate and benzoic acid.

In some embodiments, the amlexanox is formulated with a chelating agent. The chelating agent may be any pharmaceutically acceptable chelating agent. Chelating agents include ethylenediaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid and derivatives thereof. Citric acid also is known as citric acid monohydrate. Derivatives of citric acid include anhydrous citric acid and trisodiumcitrate-dihydrate. Still other chelating agents include niacinamide and derivatives thereof and sodium desoxycholate and derivatives thereof.

In some embodiments, the amlexanox is formulated with an antioxidant. The antioxidant may be any pharmaceutically acceptable antioxidant. Antioxidants are well known to those of ordinary skill in the art and include materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, and sodium sulfite. Such materials are typically added in ranges from 0.01 to 2.0%.

In some embodiments, the amlexanox is formulated with a cryoprotectant. The cryoprotecting agent may be any pharmaceutically acceptable cryoprotecting agent. Common cryoprotecting agents include histidine, polyethylene glycol, polyvinyl pyrrolidine, lactose, sucrose, mannitol, and polyols.

In some embodiments, the amlexanox is formulated with an isotonicity agent. The isotonicity agent can be any pharmaceutically acceptable isotonicity agent. This term is used in the art interchangeably with iso-osmotic agent, and is known as a compound which is added to the pharmaceutical preparation to increase the osmotic pressure, e.g., in some embodiments to that of 0.9% sodium chloride solution, which is iso-osmotic with human extracellular fluids, such as plasma. Preferred isotonicity agents are sodium chloride, mannitol, sorbitol, lactose, dextrose and glycerol.

The pharmaceutical preparation may optionally comprise a preservative. Common preservatives include those selected from the group consisting of chlorobutanol, parabens, thimerosol, benzyl alcohol, and phenol. Suitable preservatives include but are not limited to: chlorobutanol (0.30.9% W/V), parabens (0.01-5.0%), thimerosal (0.004-0.2%), benzyl alcohol (0.5-5%), phenol (0.1-1.0%), and the like.

In some embodiments, the amlexanox is formulated with a humectant to provide a pleasant mouth-feel in oral applications. Humectants known in the art include cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Amlexanox has been used as an oral tablet (e.g., 25-mg tablets) in Japan for treatment of bronchial asthma and as a topical oral paste in the United States (Aphthasol) for treatment of aphthous ulcers (canker sores). In some embodiments, either of these formulations may be used for the indications described herein. In other embodiments, different formulations are used. Aphthasol contains 5% amlexanox in an adhesive oral paste. Each gram of beige colored oral paste contains 50 mg of amlexanox in an adhesive oral paste base consisting of benzyl alcohol, gelatin, glyceryl monostearate, mineral oil, pectin, petrolatum, and sodium carboxymethylcellulose.

In some embodiments, a single dose of amlexanox or related compounds is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years). In such embodiments, compounds may be taken on a regular scheduled basis (e.g., daily, weekly, etc.) for the duration of the extended period.

The present technology generally relates to therapeutic compositions and formulations comprising amlexanox. More particularly, the present technology relates to an oral medicament, a dietary supplement, a nutritional supplement, a food supplement, a food additive, a pharmaceutical, a nutraceutical, or nutratherapeutical formulation.

The technology provided herein also includes kits for use in the instant methods. Kits of the technology comprise one or more containers comprising amlexanox, a derivative thereof, or a pharmaceutically acceptable salt thereof, and/or a second agent, and in some varations further comprise instructions for use in accordance with any of the methods provided herein. The kit may further comprise a description of selecting an individual suitable treatment. Instructions supplied in the kits of the technology are typically written instructions on a label or package insert (e.g., a paper insert included with the kit), but machine-readable instructions (e.g., instructions carried on a magnetic or optical storage disk) are also contemplated. In some embodiments, the kit is a package containing a sealed container comprising any one of the preparations described above, together with instructions for use. The kit can also include a diluent container containing a pharmaceutically acceptable diluent. The kit can further comprise instructions for mixing the preparation and the diluent. The diluent can be any pharmaceutically acceptable diluent. Well known diluents include 5% dextrose solution and physiological saline solution. The container can be an infusion bag, a sealed bottle, a vial, a vial with a septum, an ampoule, an ampoule with a septum, an infusion bag or a syringe. The containers can optionally include indicia indicating that the containers have been autoclaved or otherwise subjected to sterilization techniques. The kit can include instructions for administering the various solutions contained in the containers to subjects.

The technology also relates to methods of treatment with amlexanox. According to another aspect of the technology, a method is provided for treating a subject in need of such treatment with an effective amount of amlexanox or a salt thereof. The method involves administering to the subject an effective amount of amlexanox or salt thereof in any one of the pharmaceutical preparations described above, detailed herein, and/or set forth in the claims. The subject can be any subject in need of such treatment. In the foregoing description, the technology is in connection with amlexanox or salts thereof. Such salts include, but are not limited to, bromide salts, chloride salts, iodide salts, carbonate salts, and sulfate salts. It should be understood, however, that amlexanox is a member of a class of compounds and the technology is intended to embrace pharmaceutical preparations, methods, and kits containing related derivatives within this class. Another aspect of the technology then embraces the foregoing summary but read in each aspect as if any such derivative is substituted wherever "amlexanox" appears.

In some embodiments, a subject is tested to assess the presence, the absence, or the level of a disease (e.g., obesity and/or a related disorder, including, but not limited to insulin resistance, diabetes, steatosis, nonalcoholic steatotic hepatitis, and atherosclerosis), e.g., by assaying or measuring a biomarker, a metabolite, a physical symptom, an indication, etc., to determine the risk of or the presence of obesity and/or a related disorder, including, but not limited to insulin resistance, diabetes, steatosis, nonalcoholic steatotic hepatitis, and atherosclerosis, and thereafter the subject is treated with amlexanox based on the outcome of the test. In some embodiments, a patient is tested, treated, and then tested again to monitor the response to therapy. In some embodiments, cycles of testing and treatment may occur without limitation to the pattern of testing and treating (e.g., test/ treat, test/treat/test, test/treat/test/treat, test/treat/test/treat/ test, test/treat/treat/test/treat/treat, etc), the periodicity, or the duration of the interval between each testing and treatment phase.

EXAMPLES

Methods
  Reagents
  All chemicals were obtained from Sigma-Aldrich (Saint Louis, Mo.) unless stated otherwise. Anti-IKKε, anti-TBK1, Phospho-TBK1 (ser172), anti-IKKα/β, phospho-IKKα/β ser176/177) anti-AKT, phospho-AKT (ser473), anti-S6K, phospho-S6K (thr389), anti-S6, phospho-S6 (ser235/236), anti-IRF3, phospho-IRF3 (ser396), anti-HSL, phospho-HSL (ser563 or ser660), and anti-PPARγ antibodies were purchased from Cell Signaling (Danvers, Mass.). Anti-RalA antibody was obtained from BD Bioscience (San Jose, Calif.). Anti-UCP1 antibody was obtained from Alpha Diagnostics (San Antonio, Tex.). Enhanced chemiluminescence (ECL) reagents were purchased from NEN, Inc. EDTA-free protease inhibitor tablet was purchased from Roche Diagnostics (Indianapolis, Ind.).

During the development of embodiments of the technology provided herein, particular formulations of amlexanox were used. For example, in the experiments described, amlexanox was solubilized in NaOH, the pH of the solution was adjusted to 7.6 with 1 M Tris, pH 7.4, and the volume was adjusted with autoclaved, distilled water. The final concentration of NaOH was equimolar to the concentration of amlexanox. As a specific example, to make 20 ml of a 20 mg/ml amlexanox solution, 400 mg of amlexanox were dissolved in 10 ml of 132 mM NaOH, and then 5.2 ml of 1 M Tris, pH 7.4, and 4.8 ml of water were added. The solution of amlexanox was sterilized through a 0.2 micrometer filter. The vehicle control was made with the same buffer without amlexanox. During the development of embodiments of the technology described herein, amlexanox was administered to test subjects. For example, in the some of the experiments described amlexanox was delivered to mice by oral gavage.
  Animals and Animal Care.
  Wild type male C57BL/6 mice were fed a high fat diet consisting of 45% of calories from fat (D12451 Research Diets Inc., New Brunswick, N.J.) starting at 8 weeks of age for 12-24 weeks, while normal diet C57BL/6 controls were maintained on normal chow diet consisting of 4.5% fat (5002 Lab Diet, Philadelphia, Pa.). Diets containing ω-3 fatty acids were fed as previously described 24. Rosiglitazone treatment was administered for three weeks by addition of the compound to the diet in mice that had been on HFD for 16 weeks. Each mouse consumed on average 3.5 mg/kg rosiglitazone per day. Amlexanox was administered by daily oral gavage. For the prevention groups, amlexanox (25 mg/kg or 100 mg/kg) administration was begun concurrently with HFD feeding at 8 weeks of age. For the treatment groups, 25 mg/kg amlexanox treatment was begun at 20 weeks of age after 12 weeks of HFD. To test the effect of amlexanox withdrawal, mice in the treatment group were switched from amlexanox gavage to vehicle control after 8 weeks of amlexanox treatment. Control and ob/ob mice were maintained on a normal chow diet and gavaged with 100 mg/kg amlexanox or vehicle control beginning at 10 weeks of age. Animals were housed in a specific pathogen-free facility with a 12-hour light/12-hour dark cycle and given free access to food and water. All animal use was in compliance with the Institute of Laboratory Animal Research Guide for the Care and Use of Laboratory Animals and approved by the University Committee on Use and Care of Animals at the University of Michigan and UCSD.
  Physiological Tests and Biochemical Assays
  Particular physiological tests were used during the development of the technology provided herein. For example, in some of the experiments described below, subjects were tested for tolerance of injected glucose and insulin according to the methods described in Chiang et al. ("The protein kinase IKKepsilon regulates energy balance in obese mice", Cell (2009) 138: 961-975, incorporated herein by reference in its entirety for all purposes). In some of the experiments described below, subjects were tested for tolerance of oral glucose. In particular, mice were fasted for 6 hours before the studies. For ob/ob mice, 1.0-1.5 mg/g of glucose was gavaged into mice, and blood glucose was measured with a glucometer (e.g., OneTouch Ultra glucometer). Measurement of triglycerides, mRNA, and cytokines were performed according to the methods described in Chiang et al. (The protein kinase IKKepsilon regulates energy balance in obese mice. Cell (2009) 138: 961-975).
  Food Intake
  The remaining weight of food provided was determined daily for singly housed mice. Daily food consumption was calculated from a three-day average.
  Energy Expenditure and Respiratory Quotient
  C57B16 mice in the amlexanox treatment group were placed in metabolic cages. The University of Michigan Animal Metabolic Phenotyping Core measured oxygen consumption (VO2), carbon dioxide production (VCO2) and spontaneous motor activity during 3 consecutive days using the Comprehensive Laboratory Monitoring System (CLAMS, Columbus Instruments), an integrated open-circuit calorimeter equipped with an optical beam activity monitoring system. The respiratory quotient was calculated by dividing carbon dioxide production by oxygen consumption. The mean values for light and dark cycles were used to analyze statistical significance.
  Body Composition
  The University of Michigan Animal Phenotyping Core used NMR analysis to quantify body fat, lean body mass and fluid content in ob/ob mice and C57BL/6 mice in the amlexanox treatment group.
  Core Body Temperature
  Rectal temperature measurements were performed using a YSI 4600 Precision thermometer (YSI, Inc., Yellow Springs, Ohio).

Blood Chemistry Analysis

Blood glucose was measured by OneTouch Ultra Glucometer. Plasma from mice fasted for six hours was isolated from whole blood collected into heparinized tubes. Insulin concentrations were measured by insulin ELISA kit (Crystal Chem Inc., Downers Grove, Ill.). Leptin and adiponectin levels were measured by ELISA kits purchased from Cayman Chem Inc. (Ann Arbor, Mich.). Cytokine levels were quantified utilizing luminex technology in a multianalyte panel plate purchased from Millipore (Billerica, Mass.). Additionally, TNFα levels were measured using ELISA kits purchased from R&D Systems (Minneapolis, Minn.).

Glucose and Insulin Tolerance Tests

For glucose tolerance tests, after a six-hour fast mice were orally gavaged with glucose at a dose of 1.5 g/kg (C57BL/6 mice) or 1.2 g/kg (ob/ob mice). For insulin tolerance tests, mice were fasted for three hours then given an intraperitoneal injection of insulin (1.2 units/kg for C57BL/6 mice and 2.0 units/kg for ob/ob mice). Blood glucose was measured at basal, 15, 30, 45, 60, 90, 120 and 180 minutes from tail blood using the One Touch Ultra glucometer (Lifescan, Milpitas, Calif.).

Liver Lipid Content

Liver lipids were isolated as previously described (Norris et. Al. 2003) and the triglyceride levels were measured by Triglyceride Reagent kit.

Liver Glycogen Content

Determination of glycogen in liver was performed as follows. Briefly, liver tissue was digested in a 30% potassium hydroxide solution, and then glycogen was precipitated using ethanol. After three washes to remove any traces of glucose, glycogen was digested by addition of amyloglucosidase. Released glucose was quantified using a colorimetric kit (Wako, Richmond, Va.).

Stromal Vascular Fraction (SVF) and Adipocyte Isolation

Excised WAT was digested in PBS containing 1% BSA and 1 mg/mL type II collagenase for 30 minutes at 37° C. with gentle agitation. The cell suspension was filtered through a 100 µm filter and then spun at 700×g for 5 minutes to separate floating adipocytes from SVF pellet. Floating adipocytes were washed twice with PBS containing 1% BSA and the SVF pellet collected after each wash.

Western Analysis

Tissues were homogenized in lysis buffer (50 mM Tris, pH 7.5, 5 mM EDTA, 250 mM sucrose, 1% NP40, 2 mM DTT, 1 mM sodium vanadate, 100 mM NaF, 10 mM $Na_4P_2O_7$, and freshly added protease inhibitor tablet), then incubated for one hour at 4° C. Crude lysates were then centrifuged at 14,000×g for 15 minutes twice and the protein concentration was determined using BioRad Protein Assay Reagent. Samples were diluted in sodium dodecyl sulfate (SDS) sample buffer. Bound proteins were resolved by SDS-polyacrylamide gel electrophoresis and transferred to nitrocellulose membranes (Bio-Rad, Hercules, Calif.). Individual proteins were detected with the specific antibodies and visualised on film using horseradish peroxidase-conjugated secondary antibodies (Bio-Rad, Hercules, Calif.) and Western Lightning Enhanced Chemiluminescence (Perkin Elmer Life Sciences, Waltham, Mass.).

Histochemistry

Tissues were fixed in formalin for 3 days. Histology was performed by the University of Michigan Cancer Center Research Histology Laboratory.

Gene Expression Analysis

Mouse tissues were isolated, rinsed in Phosphate Buffered Saline (PBS), frozen in liquid nitrogen and stored at −80° C. until extraction. Total RNA was extracted from Liver, WAT and BAT tissues as well as differentiated 3T3-L1 cells using the RNeasy Lipid Tissue Kit (Qiagen, Valencia, Calif.) according to the manufacturer's instructions with the inclusion of a DNase digestion step. Total RNA was extracted from BMDM and SVF cells using the RNeasy Kit (Qiagen, Valencia, Calif.) with a DNase step. The Superscript First-Strand Synthesis System for RTPCR (Invitrogen, Grand Island, N.Y.) was used with random primers for reverse transcription. Realtime PCR amplification of the cDNA was performed on samples in triplicate with Power SYBR Green PCR Master Mix (Applied Biosystems, Carlsbad, Calif.) using the Applied Biosystems 7900HT Fast Realtime PCR System. Adrp or GAPDH were chosen as the internal control for normalization after screening several candidate genes; their expression was not significantly affected by experimental conditions. Data was analyzed using the 2-ΔΔCT method, and statistical significance was determined using the unpaired heterocedastic Student's t-test with one averaged sample value per mouse.

Lipid Oxidation Rate

Intrascapular BAT was excised and placed in DMEM with 2% BSA with and without 5 µM amlexanox then incubated at 37° C. for 1 hour, after which the media was changed to DMEM with 2% BSA, 0.25 mM carnitine, 0.2 mM palmitic acid and 3H-palmitic acid and incubated for one more hour at 37° C. and then the media collected, and the aqueous faction isolated. Lipid oxidation was determined by the conversion of 3H-palmitic acid to 3H2O.

IKKε and TBK1 In Vitro Kinase Assays

In vitro kinase assays were performed by incubating purified kinase (IKKε or TBK1) in kinase buffer containing 25 mM Tris (pH7.5), 10 mM $MgCl_2$, 1 mM DTT, and 10 µM ATP for 30 minutes at 30° C. in the presence of 0.5 µCi γ-[32P]-ATP and 1 µg myelin basic protein (MBP) per sample as a substrate. Kinase reaction was stopped by adding 4× sodium dodecyl sulfate (SDS) sample buffer and boiling for 5 minutes at 95° C. Supernatants were resolved by SDS-polyacrylamide gel electrophoresis, transferred to nitrocellulose, and analyzed by autoradiography using a Typhoon 9410 phosphorimager (GE Lifesciences, Piscataway, N.J.). The bands were quantified using ImageQuant.

IKKε and TBK1 Immune-Complex Kinase Assay

Liver and White adipose tissues were collected from C57BL/6 mice on normal chow or high fat diet. Tissues were homogenized using Dounce homogenizer with lysis buffer containing 50 mM Tris (pH7.5), 150 mM NaCl, 2 mM EDTA, 5 mM NaF, 25 mM β-glycerophosphate, 1 mM sodium orthovanadate, 10% glycerol, 1% TritonX-100, 1 mM DTT, and 1 mM PMSF in the presence of protease inhibitors (Roche Diagnostics). Tissue cell lysates were incubated for 1 hour at 4° C. and cleared by spinning at 13,000 rpm for 15 minutes at 4° C. in a table-top centrifuge. Each 1 mg of lysate was subjected to immunoprecipitation using 5 µl of rabbit-polyclonal antibody against TBK1 or IKKε for 1.5 hours at 4° C. Immunocomplexes were harvested by incubation with ProtA beads (Roche Diagnostics, Indianapolis, Ind.) for 2 hours at 4° C. Immunoprecipitates were extensively washed once with lysis buffer and three times with wash buffer containing 20 mM Hepes (pH 7.4), 50 mM NaCl, 20 mM β-glycerophosphate, 1 mM sodium orthovanadate, 5 mM NaF, 10 mM MgCl2, and 1 mM DTT. An in vitro kinase assay using the immunoprecipitated kinases was performed as described above. Relative levels of MBP phosphorylation were detected by autoradiograph and normalized to the levels of IKKε or TBK1 kinase detected in the immunoprecipitate by immunoblotting.

Cell Culture and Transfection

3T3-L1 fibroblasts (American Type Culture Collection, Manassas, Va.) were cultured and differentiated using standard methods known in the art. Cells were routinely used within 7 days after completion of the differentiation process; only cultures in which >90% of cells displayed adipocyte morphology were used. 3T3-L1 adipocytes were serum starved with 0.5% fetal bovine serum (FBS) in Dulbecco's modified eagle medium (DMEM) prior to treatment. TNFα treatments (50 ng/mL unless otherwise noted) were performed during the 24 hour prior to harvest, after pretreatment with IKKβ inhibitor compound VIII (EMD Biosciences, Philadelphia, Pa.) for 1 hour where indicated. 3T3-L1 adipocytes were pre-treated for 1 hour with amlexanox at the given concentrations, then treated with 20 μg/ml of poly I:C for 1 hour. Alternatively, 3T3-L1 adipocytes were treated with 50 μM forskolin for 15 minutes, after a 30 minute amlexanox pretreatment. Cells were treated with or without 10 nM of insulin for 15 minutes. RAW264.7 cells were serum starved with 0.5% FBS DMEM media and pre-treated with or without Cay-10576 (Cayman Chemical, Ann Arbor, Mich.). The cells were then treated with LPS (0.5 μg/ml) or poly I:C (50 μg/ml) for 1 hour. Cells were harvested for total RNA and analyzed by real-time PCR Cell lysates were resolved on SDS-PAGE and analyzed by immunoblot using the indicated antibodies.

Statistics

During the development of embodiments of the technology provided herein, statistical analyses were used to evaluate data. For instance, data were assessed using the Student T-test. In figures showing data collected during development of the technology, data with a p value less than 0.05 are marked with a single asterisk (*) and data with a p value less than 0.01 are marked with a double asterisk (**). In addition, in figures showing data collected during the development of the technology, error bars indicate the standard error of the mean (S.E.M.) for the data.

Molecular Modeling of Amlexanox in the IKKε ATP Binding Site.

The structure of IKKε was determined by homology modeling using the high resolution crystal structure of the kinase domain of mitogen-activated protein kinase p38 (sequence identity 56%) as the template structure (PDB accession 1P38). The amlexanox complex with IKKε was modeled on the basis of the crystal structure of MAP kinase p38 complexed to an ATP competitive inhibitor (2-aminophenylaminodibenzosuberone) (PDB accession 3ZYA).

Example 1

During the development of embodiments of the technology provided herein, it was discovered that amlexanox blocked IKKε and TBK1 activity. As shown in FIG. 1, the kinase activity of both IKKε and TBK1 decreased with increasing doses of amlexanox. Analysis of the dose-response curves shows that amlexanox blocked IKKε and TBK1 activity with an $IC_{50}$ of approximately 1-2 μm. Amlexanox had no effect on IKKα or β at these concentrations, and did not block any others from a broad panel of kinases representing most families.

Example 2

During the development of embodiments of the technology provided herein, it was discovered that amlexanox competes with ATP for binding to IKKe. FIG. 2 shows a double-reciprocal plot of amlexanox activity versus ATP concentration in the presence of three different amlexanox concentrations. Phosphorylation of myelin basic protein (MBP) by IKKε was measured at three different amlexanox concentrations and three different ATP concentrations. The reciprocal of the measured activity was plotted versus the reciprocal of the ATP concentration. With increasing amlexanox concentration, the slope of the line fitting the data changes but not the y-intercept, consistent with a competitive mode of enzyme inhibition.

TBK1 and IKKε share 65% sequence similarity, and are 72% identical in the ATP binding region. Inhibition of IKKε or TBK 1 by amlexanox was competitive for its substrate ATP, indicating that it interacts with the enzymes in the ATP-binding site. This is consistent with a model of the compound docked in the presumed ATP binding pocket of IKKε (see below), based on the structure of p38.

Example 3

During the development of embodiments of the technology provided herein, computer modeling was used to examine the interaction of amlexanox with IKKe. The presumed ATP binding site of IKKe can has the appropriate size and geometry to accommodate the amlexanox molecule.

Example 4

Figure 3:
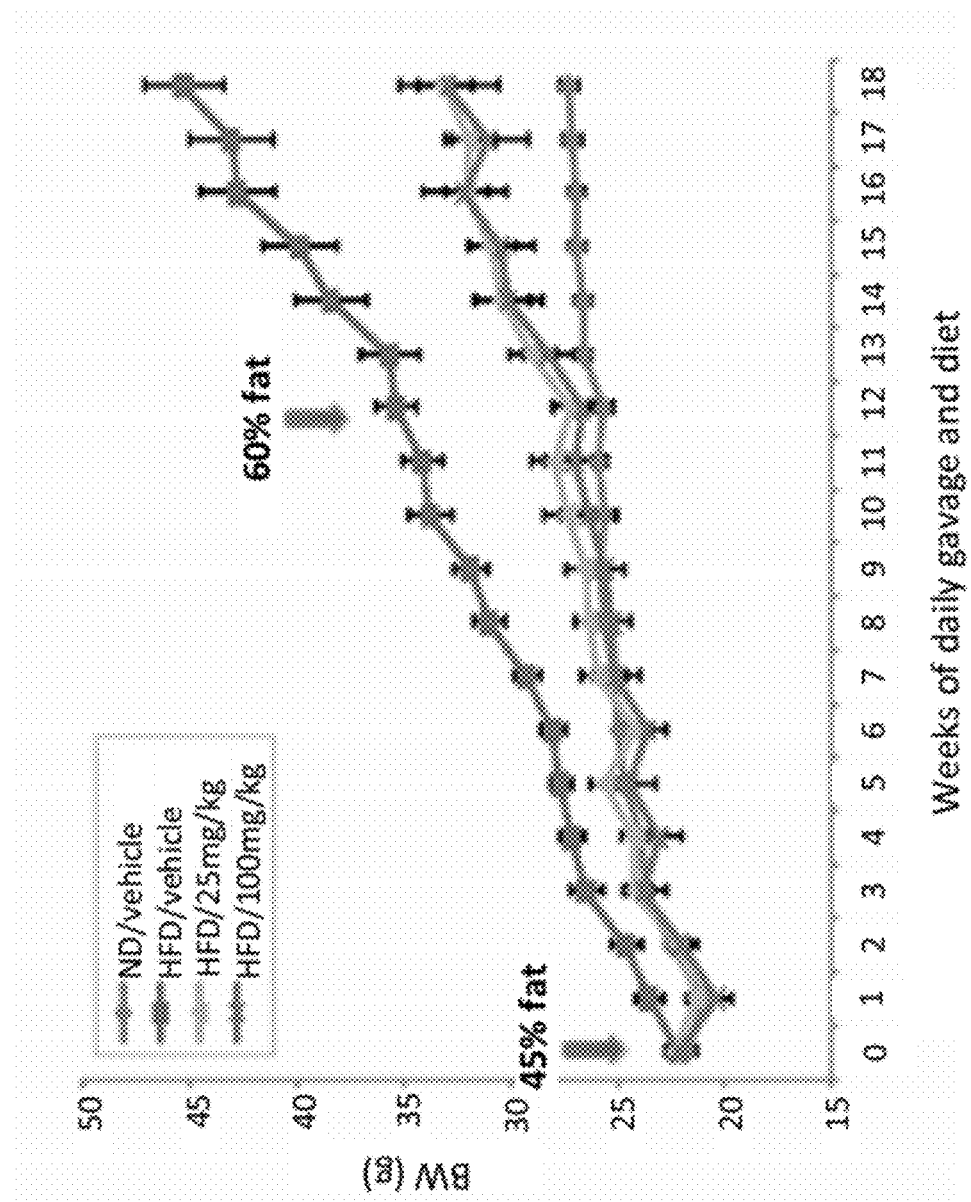
FIG. 3 shows a plot of body weight versus time for mice fed a high-fat diet and treated with amlexanox.

During the development of embodiments of the technology provided herein, it was discovered that amlexanox prevents weight gain in mice fed a high-fat diet. C57B1/6 mice were fed a diet of 45% fat and subject to daily gavage with 25 or 100 mg/kg amlexanox. Controls were mice fed normal chow and subject to daily vehicle gavage and mice fed high-fat diets and subject to daily vehicle gavage. After 12 weeks on the 45% fat diet, mice were challenged with a 60% fat diet. Mouse body weight was monitored throughout the experiment for 18 weeks. As shown in FIG. 3, treatment of animals with either dose of amlexanox prevented weight gain produced by a high-fat diet. After switching mice to the 60% fat diet, amlexanox still prevented substantial weight gain at both doses.

Figure 4:
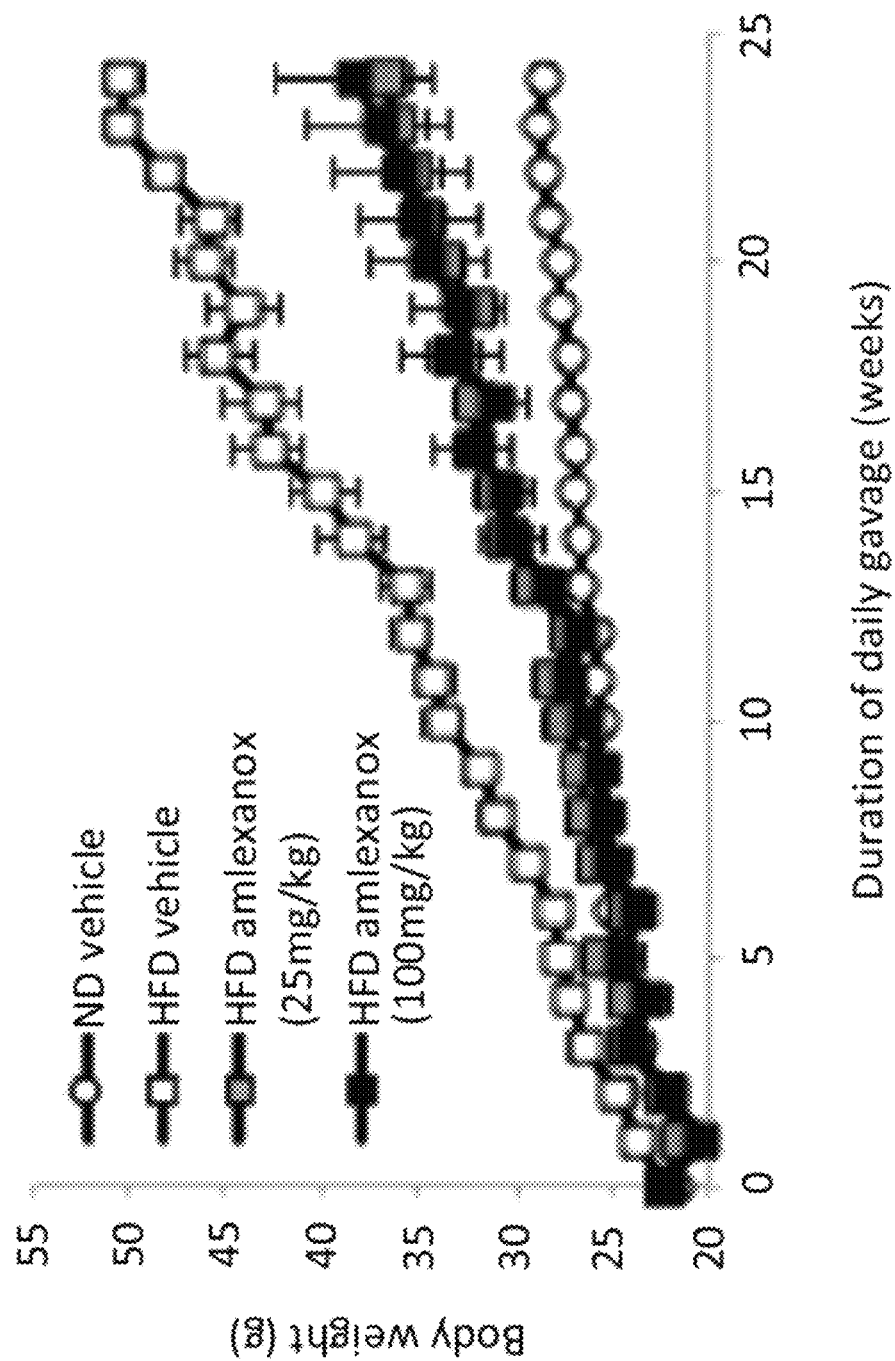
FIG. 4 shows a plot of body weight versus time for mice fed a high fat diet (HFD) and gavaged with amlexanox at 25 mg/kg (grey squares) or 100 mg/kg (black squares) or with vehicle control (white squares=HFD, white circles=ND). Initiation of gavage in the preventative group coincided with high fat diet (HFD) feeding at 8 weeks of age (n=5 per group).

In additional experiments, C57B1/6 mice were given a diet of 45% fat, and subject to daily gavage with a vehicle control, 25 mg/kg, or 100 mg/kg amlexanox. Weights of the mice were monitored as shown in FIG. 4. Normal chow-fed mice on vehicle gavage were used as a lean control. Treatment of animals with either dose of amlexanox prevented the weight gain produced by high fat diet; drug-treated mice maintained weights equivalent to those of control diet mice throughout 12 weeks. There was no effect of the drug on food intake, either at the beginning or end of the study Example 5

During the development of embodiments of the technology provided herein, it was discovered that amlexanox produced weight loss after diet-induced obesity had been established. Mice were fed a 45% high-fat diet for 12 weeks, and then treated with 25 mg/kg of amlexanox for 3 weeks. Control mice were fed a 45% high-fat diet for 12 weeks, and then treated with vehicle control for 3 weeks. As shown in FIGS. 5a, amlexanox produced a 10-g weight loss after only 4 weeks of treatment. Amlexanox produced this effect without a simultaneous reduction in food intake (see FIG. 5b).

To determine whether the effects of the drug were reversible, amlexanox treatment was stopped after 8 weeks of treatment, after which mice were instead given vehicle control. Mice quickly regained the weight that had been lost, returning to control weights 6-8 weeks after treatment was stopped (FIG. 5c). Weight loss during the treatment phase was accompanied by more than a 6 gram reduction in overall mass of adipose tissue, as well as an 80% decrease in fasting levels of leptin, whereas serum triglycerides, free fatty acids and cholesterol were unchanged (FIG. 5d).

Figure 5:
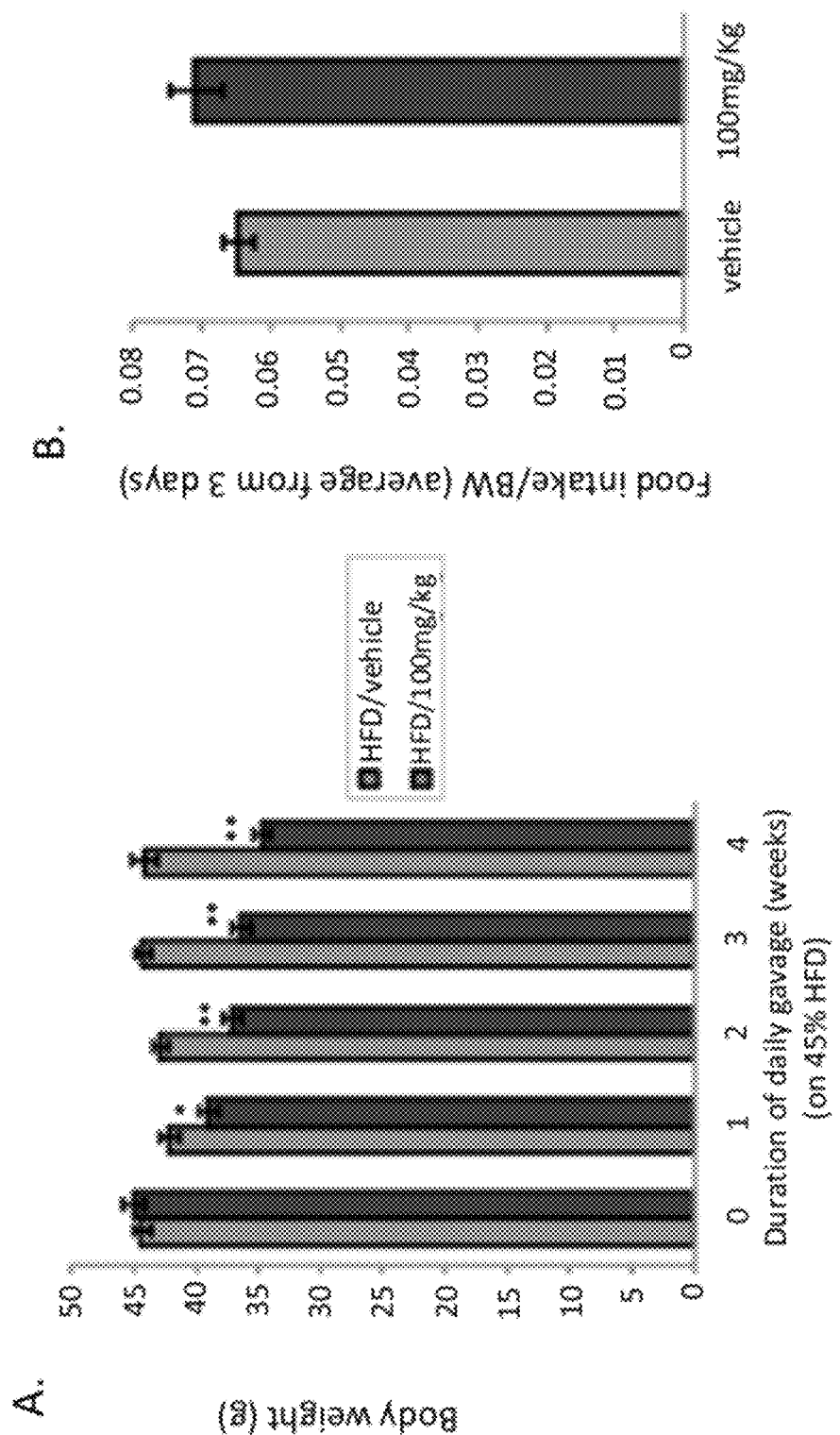
FIG. 5A shows a plot of body weight versus time (duration of gavage) for mice fed a high-fat diet and treated with amlexanox.
FIG. 5B shows a plot of food intake during treatment for mice fed a high-fat diet and then treated with amlexanox.
FIG. 5C shows a plot of body weight for mice treated preventatively with 25 mg/kg amlexanox (black squares) or vehicle control (white squares) for 8 weeks, after which the withdrawal group (black Xs) was switched to vehicle control treatment (n=7 per group).
FIG. 5D sows a plot of total (left panel) and relative (right panel) fat and lean body mass of mice in the treatment group. ND vehicle control: light grey bars, ND 25 mg/kg amlexanox: dark grey bars, HFD vehicle control: white bars and HFD 25 mg/kg amlexanox: black bars. (n=4 for ND groups, n=8 for HFD groups).
Figure 5:
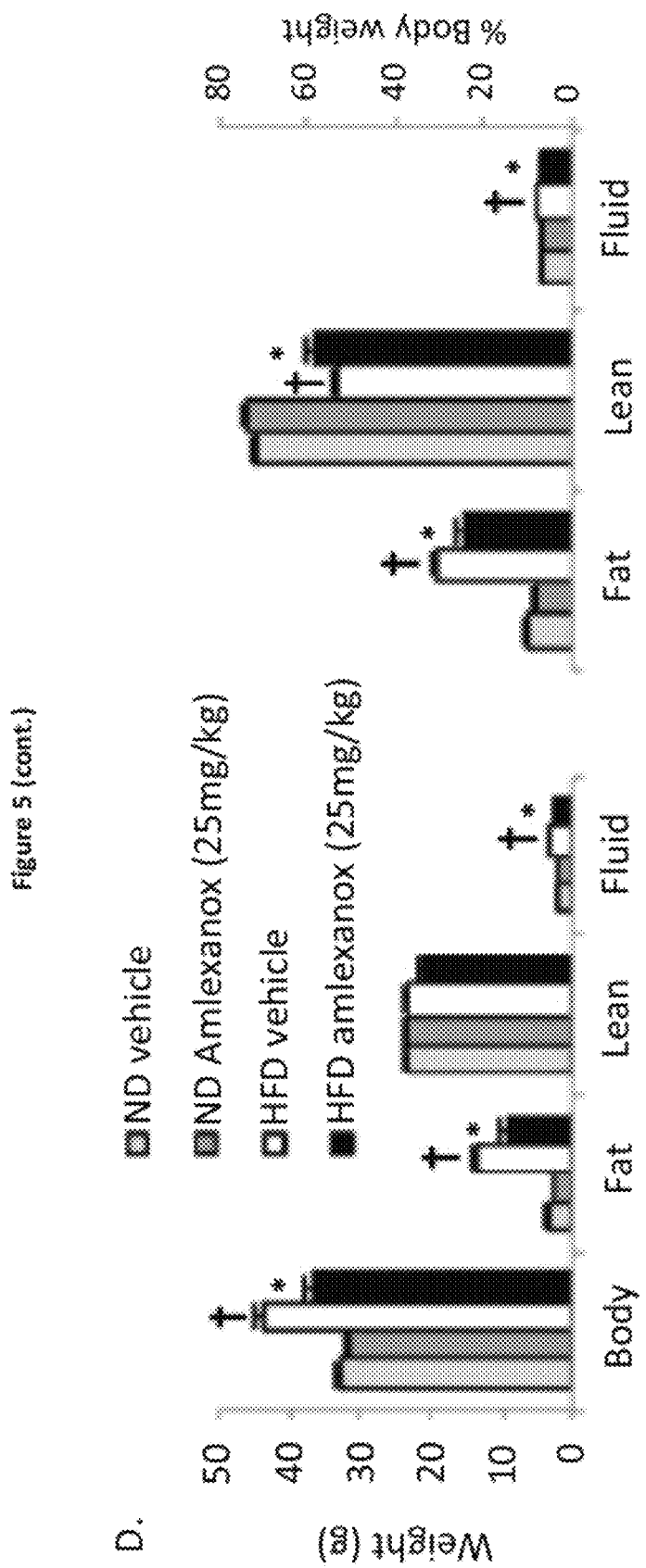

In FIG. 5, data marked with a single asterisk (*) have a p value of less than 0.05 and data marked with a double asterisk (**) have a p value of less than 0.01.

Example 6

Figure 6:
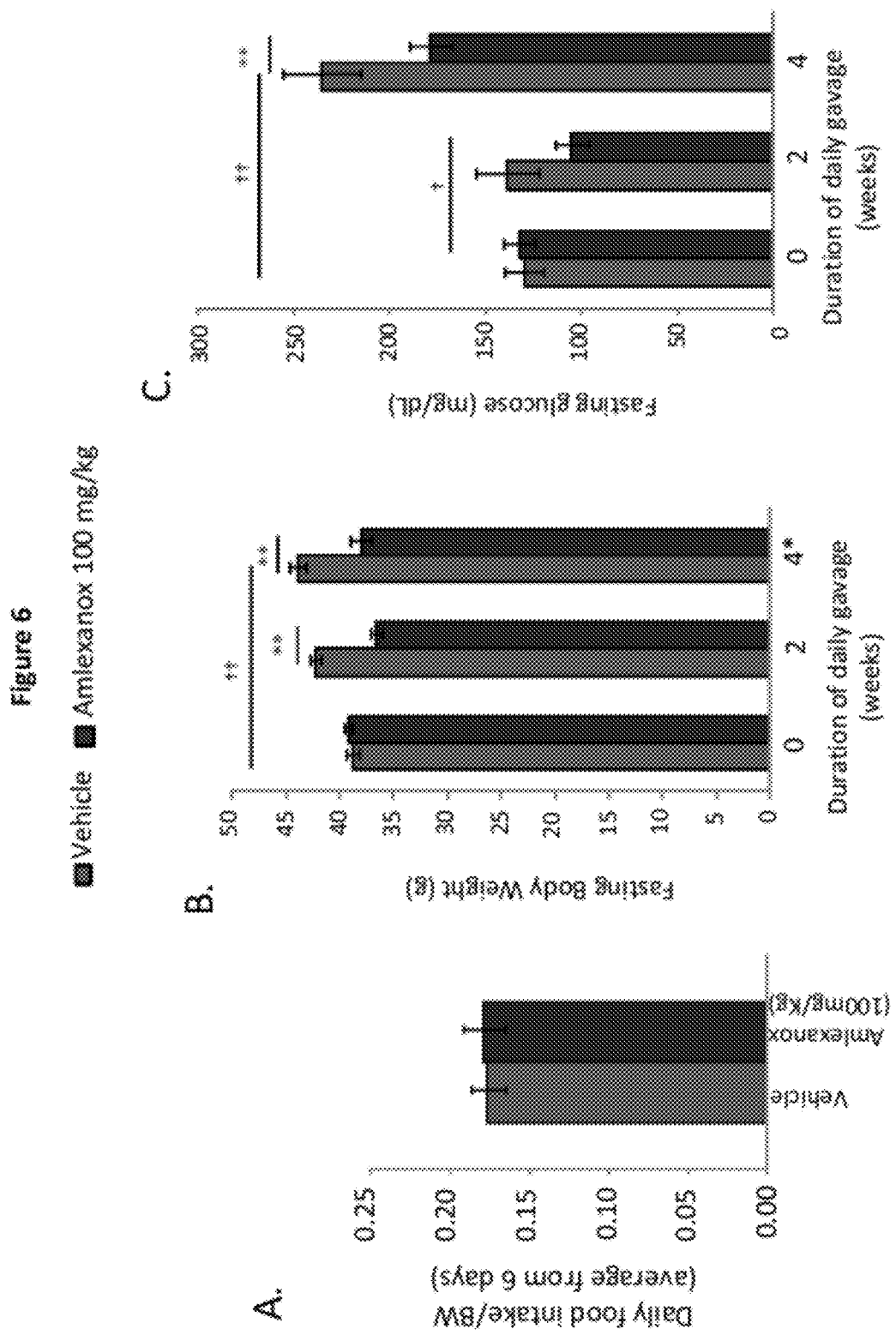
FIG. 6A shows a plot of food intake for Ob/ob mice treated with amlexanox.
FIG. 6B shows a plot of body weight versus duration of treatment for Ob/ob mice treated with amlexanox.
FIG. 6C shows a plot of fasting glucose levels versus duration of treatment for Ob/ob mice treated with amlexanox.
FIG. 6D shows a plot of oral glucose tolerance. ND vehicle control (white circles), HFD vehicle control (white squares) HFD 25 mg/kg amlexanox (black squares). (n=5 per group).
FIG. 6E shows a plot of fasting blood glucose and serum insulin levels in mice: ND vehicle control (grey bars), HFD vehicle control (white bars) and HFD 25 mg/kg amlexanox treated (black bars). (n=8 per group).
FIG. 6F shows a plot of insulin tolerance. ND vehicle control (white circles), HFD vehicle control (white squares) HFD 25 mg/kg amlexanox (black squares). (n=8 per group).
Figure 6:
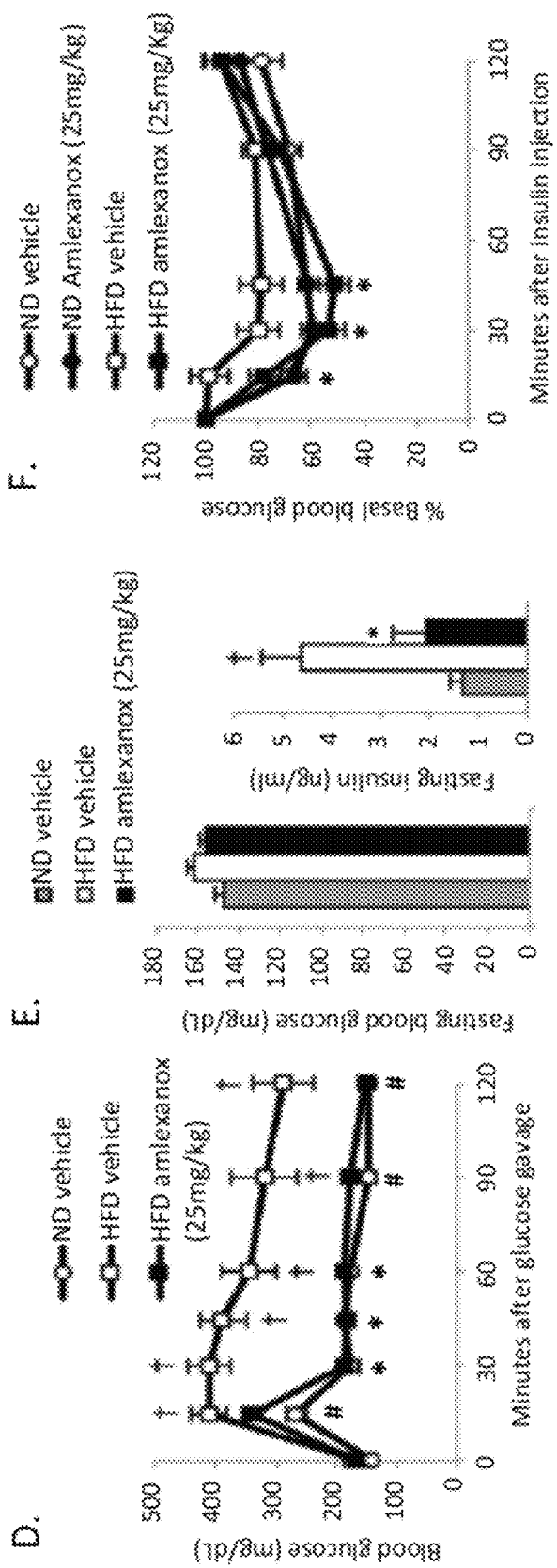

During the development of embodiments of the technology provided herein, it was discovered that amlexanox treatment produces weight loss and improved glucose tolerance and insulin sensitivity in Ob/ob mice. Ob/ob mice are genetically obese due to loss of the gene encoding the satiety factor leptin. Ob/ob mice were treated with 100 mg/kg amlexanox or with vehicle as a control, and mouse body weight was monitored (FIG. 6b). Although treatment had no effect on food intake (FIG. 6a), amlexanox produced a 7-8 g weight loss after 4 weeks of treatment and produced a 25% reduction in fasting glucose levels (FIG. 6c). Amlexanox also caused a significant decrease in adipose tissue mass in these mice, and an increase in circulating adiponectin levels. In FIG. 6, data marked with a double asterisk (**) have a p value of less than 0.01.

In additional experiments, glucose homeostasis was evaluated in a model of obese insulin resistance. Diet induced obese mice were treated with 25 mg/kg amlexanox or vehicle control for 8 weeks either before or after obesity was established, followed by assessment of metabolic parameters. Mice treated with amlexanox concurrently with high fat diet had dramatically improved glucose tolerance, with an approximate 30-40% reduction in the area under the curve for glucose (FIG. 6d). Diet-induced obesity caused fasting blood glucose and serum insulin levels to rise significantly (FIG. 6e). Treatment of mice with amlexanox after established Diet-induced obesity reversed elevations in fasting serum insulin caused by high fat diet, suggesting improved insulin sensitivity. Insulin tolerance tests showed that the drug produces an improvement in insulin sensitivity. Amlexanox dramatically improved insulin sensitivity in mice with established diet-induced obesity, as indicated by a restoration in insulin responsiveness to normal diet levels (FIG. 6f).The drug did not affect insulin sensitivity in normal diet-fed mice.

Taken together, these effects are comparable to what is observed with established insulin sensitizing drugs such as the thiazolidinediones or metformin, demonstrating that amlexanox acts as an insulin sensitizer.

Example 7

During the development of embodiments of the technology provided herein, it was discovered that amlexanox treatment results in increased glucose tolerance. Over an 8-week period, Ob/ob mice were treated with 100 mg/kg amlexanox or vehicle as a control and tested for oral glucose tolerance. Over the 8-week experiment, glucose tolerance was dramatically improved in the drug-treated mice as demonstrated by the 30-40% reduction in the area under the curve for drug-treated mice relative to control mice (FIG. 7a).

Figure 7:
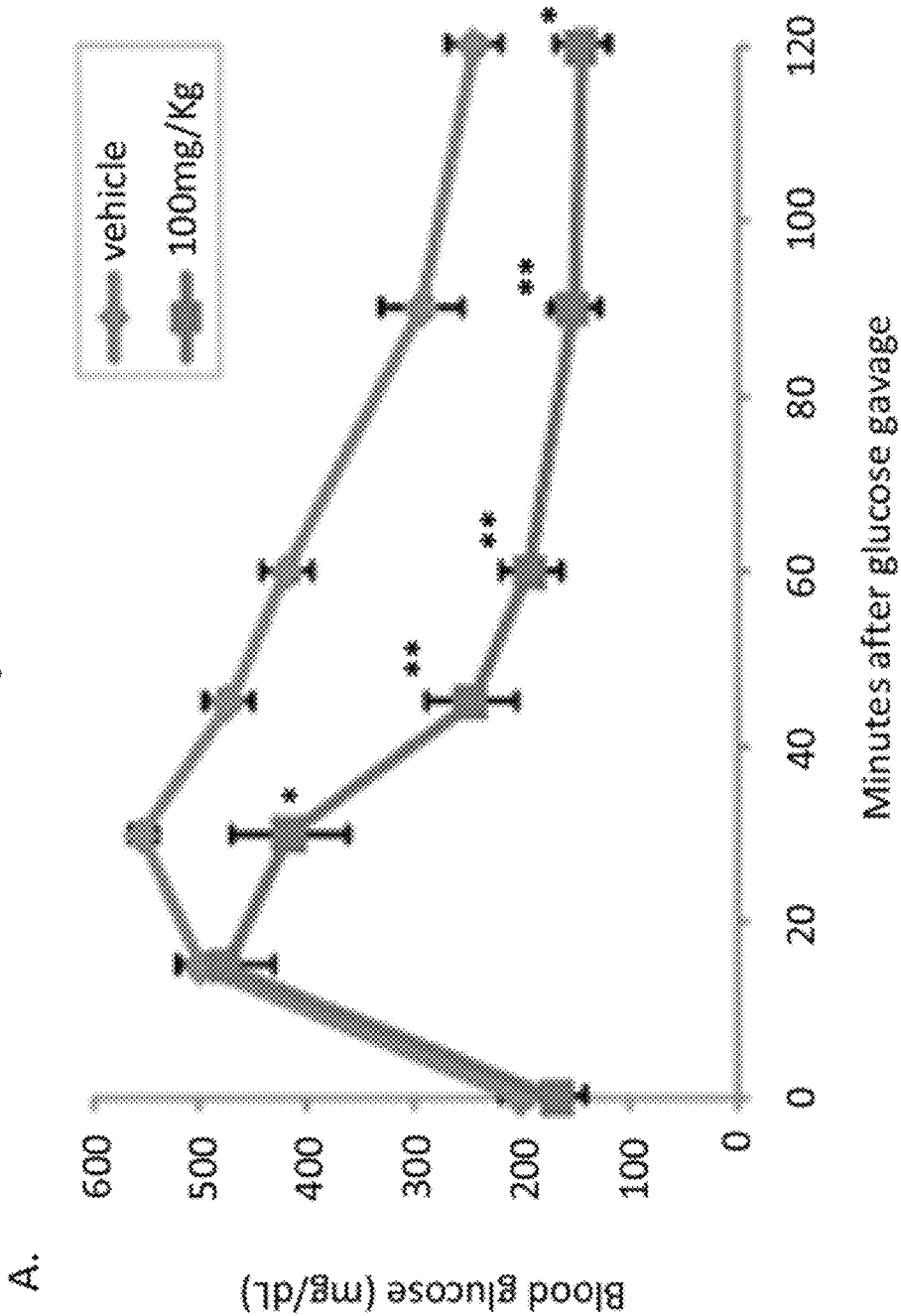
FIG. 7A shows a plot of blood glucose level as a function of time after glucose gavage for amlexanox-treated Ob/ob mice.
FIG. 7B shows a plot of blood glucose level as a function of time after glucose injection for amlexanox-treated Ob/ob mice.

Similar experiments tested tolerance to injected glucose. Over a 5-week period, Ob/ob mice were treated with 100 mg/kg amlexanox or vehicle as a control and tested for tolerance to injected glucose. As seen in FIG. 7b, amlexanox-treated mice demonstrated faster clearance of blood glucose after injection. In FIG. 7, data marked with a single asterisk (*) have a p value of less than 0.05 and data marked with a double asterisk (**) have a p value of less than 0.01.

Example 8

Figure 8:
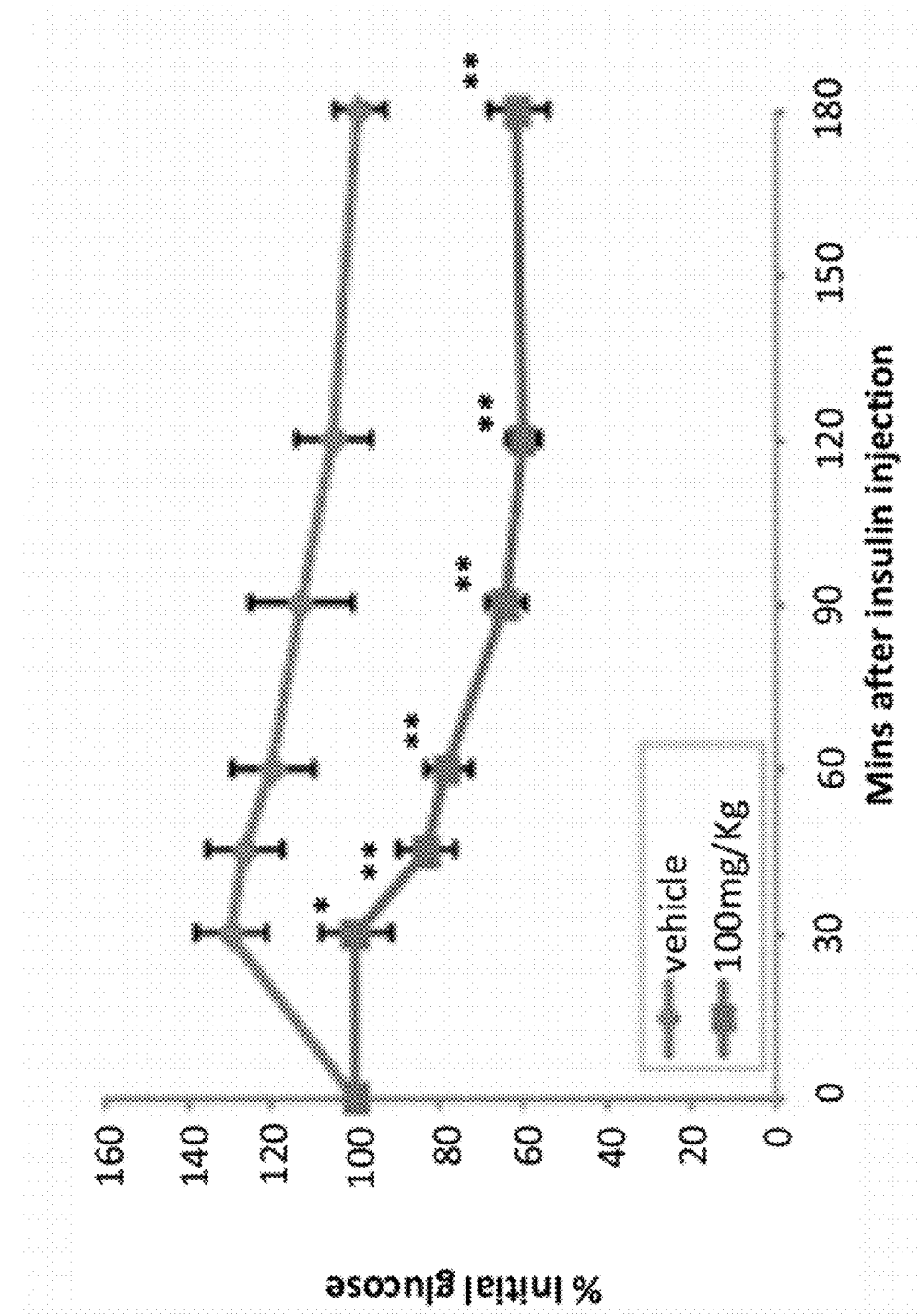
FIG. 8 shows a plot of the percent of initial glucose remaining as a function of time after insulin injection for amlexanox-treated Ob/ob mice.

During the development of embodiments of the technology provided herein, it was discovered that amlexanox treatment results in increased sensitivity to insulin. Over an 8-week period, Ob/ob mice were treated with 100 mg/kg amlexanox or vehicle as a control and tested for responsiveness to injected insulin. Over the 8-week experiment, insulin sensitivity was dramatically improved in the drug-treated mice as demonstrated by the restoration in insulin responsiveness for drug-treated mice relative to control mice (FIG. 8). The effects seen in Examples 7 and 8 are similar to the effects seen in conventional insulin sensitization therapies. In FIG. 8, data marked with a single asterisk (*) have a p value of less than 0.05 and data marked with a double asterisk (**) have a p value of less than 0.01.

Example 9

During the development of embodiments of the technology provided herein, it was discovered that amlexanox improved hepatic steatosis in mice fed a high-fat diet. Diet induced obese mice were treated with 25 mg/kg amlexanox or vehicle control for 8 weeks. Mice were then sacrificed and livers were examined. The hepatomegaly normally observed in high fat fed mice was largely reversed by the drug, with a greater than 20% reduction in liver weight (FIG. 9a). Moreover, triglyceride content in liver was reduced more than 50% in the amlexanox-treated mice compared to vehicle control (FIG. 9a). Additionally, hepatic glycogen levels, which are elevated in high fat diet-fed mice, were lower in mice treated with amlexanox as compared to control high fat diet-fed mice (FIG. 9b). Interestingly, these beneficial reductions in hepatic lipids were reversed in livers from mice that were taken off drug and continued on high fat diet, as detected in stained tissue sections.

Figure 9:
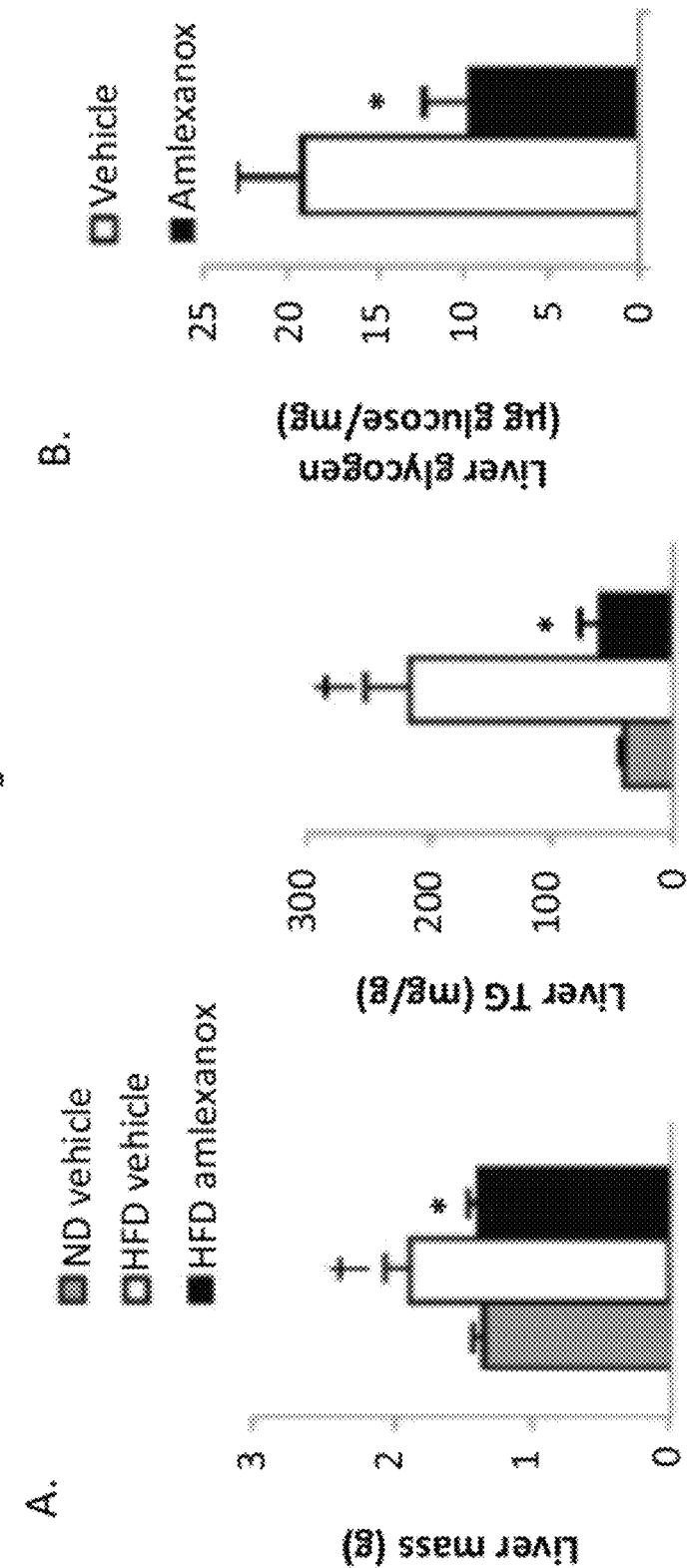
FIG. 9A shows plots of liver mass and liver triglycerides for amlexanox-treated Ob/ob mice.
FIG. 9B shows a plot of liver glycogen for amlexanox-treated Ob/ob mice.
FIG. 9C shows a plot of liver weight relative to mouse body weight for amlexanox-treated Ob/ob mice.
FIG. 9D shows a plot of liver triglycerides for amlexanox-treated Ob/ob mice.

IKKe knockout mice do not develop a fatty liver, also known as hepatic steatosis, on a high-fat diet when compared to control mice. To determine if amlexanox could mimic this effect of IKKe gene deletion, Ob/ob mice were treated with 100 mg/kg amlexanox or vehicle control for 14 weeks. At the end of the treatment period, mice were sacrificed and livers were examined (FIG. 9c). The hepatomegaly normally observed in ob/ob mice was largely reversed by the drug, with a greater than 20% reduction in liver weight (FIG. 9c). In addition, triglyceride contents in livers were reduced by more than 50% in the amlexanox-treated mice (FIG. 9d). In FIG. 9, data marked with a double asterisk (**) have a p value of less than 0.01.

Example 10

During the development of embodiments of the technology provided herein, it was discovered that amlexanox treatment results in reduced size of triglyceride droplets in the liver. Ob/ob mice were treated with 100 mg/kg amlexanox or vehicle control for 14 weeks. At the end of the treatment period, mice were sacrificed and livers were examined using H & E staining. In control Ob/ob mice, large lipid droplets were apparent. These were largely disseminated in livers from amlexanox-treated mice, consistent with the reduced triglycerides and liver weight observed in Example 8.

In addition, diet induced obese mice were treated with 25 mg/kg amlexanox or vehicle control for 8 weeks. Mice were then sacrificed and livers were examined by H & E staining. In diet induced obese mice treated with vehicle control, large lipid droplets were apparent. These were largely disseminated in livers from amlexanox-treated mice, consistent with the major reduction in triglycerides, glycogen and liver weight.

Example 11

During the development of embodiments of the technology provided herein, it was discovered that amlexanox treatment results in the reduced expression of certain key lipogenic genes. Ob/ob mice were treated with 100 mg/kg amlexanox or vehicle control for 14 weeks. At the end of the treatment period, mice were sacrificed and liver mRNA levels were measured for acetyl CoA carboxylase (ACC), fatty acid synthase (FAS), and stearyl CoA desaturase (SCD1). As shown in FIG. 10, the expression of these genes was reduced in amlexanox-treated mice compared to vehicle-treated control mice. In FIG. 10, data marked with a single asterisk (*) have a p value of less than 0.05 and data marked with a double asterisk (**) have a p value of less than 0.01. Similar experiments in mice with diet induced obesity showed that genetic measures of hepatosteatosis were similarly reduced.

Example 12

Figure 11:
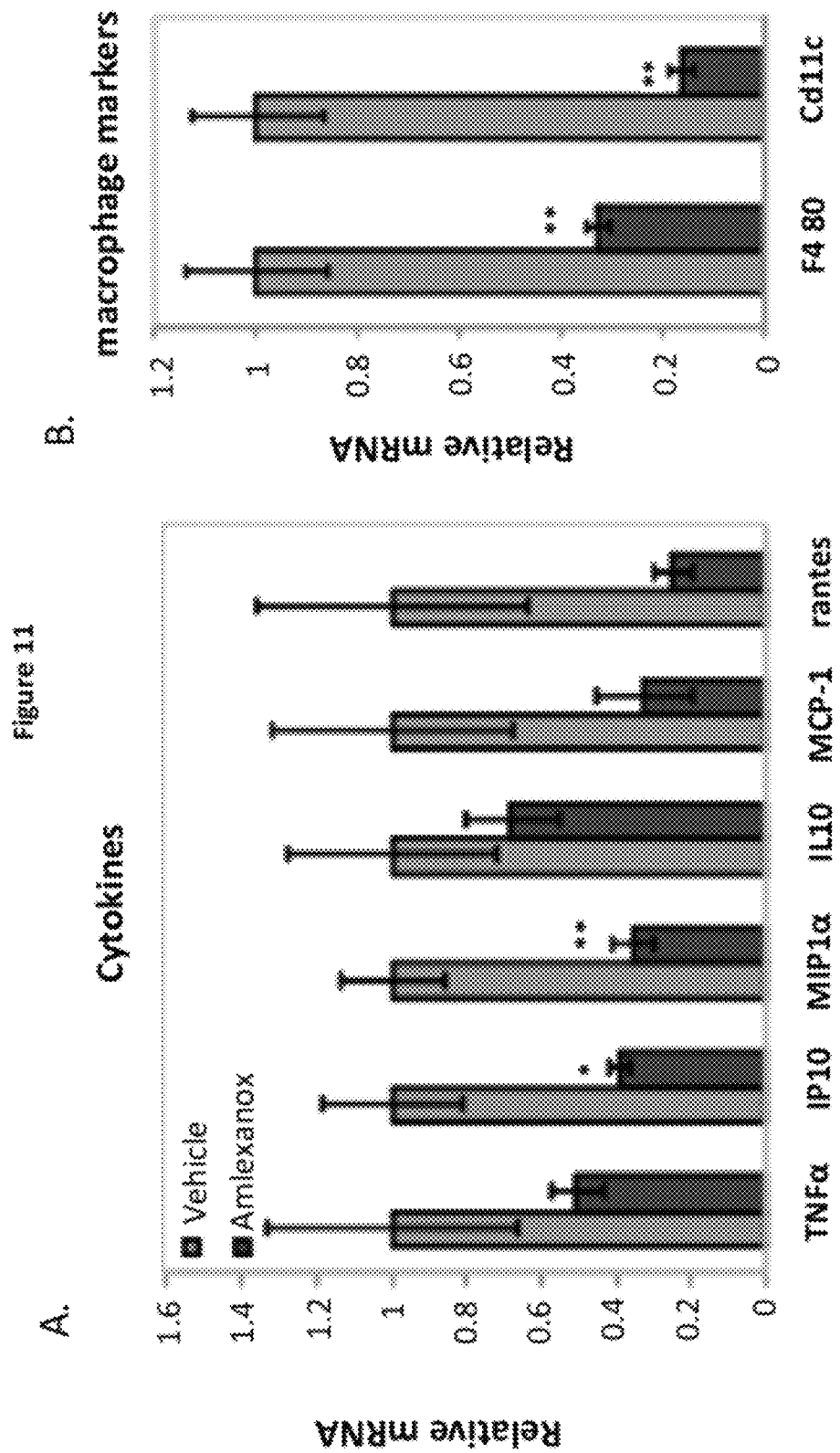
FIG. 11A shows relative mRNA levels for inflammatory genes expressed in the livers of amlexanox-treated Ob/ob mice.
FIG. 11B shows relative mRNA levels for macrophage marker genes expressed in the livers of amlexanox-treated Ob/ob mice.

During the development of embodiments of the technology provided herein, it was discovered that amlexanox treatment results in the reduced expression of several inflammatory cytokines in the liver (FIGS. 11a). Ob/ob mice were treated with 100 mg/kg amlexanox or vehicle control for 14 weeks. At the end of the treatment period, mice were sacrificed and liver mRNA levels were measured for TNFα, IL-10, MIP1α, Rantes, and markers of macrophage infiltration (F4/80 and Cd11c). As shown in FIGS. 11a and 11b, the expression of these genes was reduced in amlexanox-treated mice compared to vehicle-treated control mice. In FIG. 11, data marked with a single asterisk (*) have a p value of less than 0.05 and data marked with a double asterisk (**) have a p value of less than 0.01.

Example 13

During the development of embodiments of the technology provided herein, it was discovered that amlexanox reduced chronic inflammation in the adipose tissue of Ob/ob mice. Ob/ob mice were treated with 100 mg/kg of amlexanox or vehicle as a control for 12 weeks. At the conclusion of treatment, epididymal fat tissue was examined by H & E staining. Amlexanox treatment markedly reduced the infiltration of inflammatory macrophages in adipose tissue compared to control, vehicle-treated mice. Amlexanox-dependent reduction in the appearance of macrophages in crown like structures was accompanied by a marked reduction in the levels of mRNAs in adipose tissue encoding key inflammatory genes TNFα, MIP1α, MCP-1, IL-10, Rantes, F4/80, and CD11c (FIGS. 12a and 12b).

Figure 12:
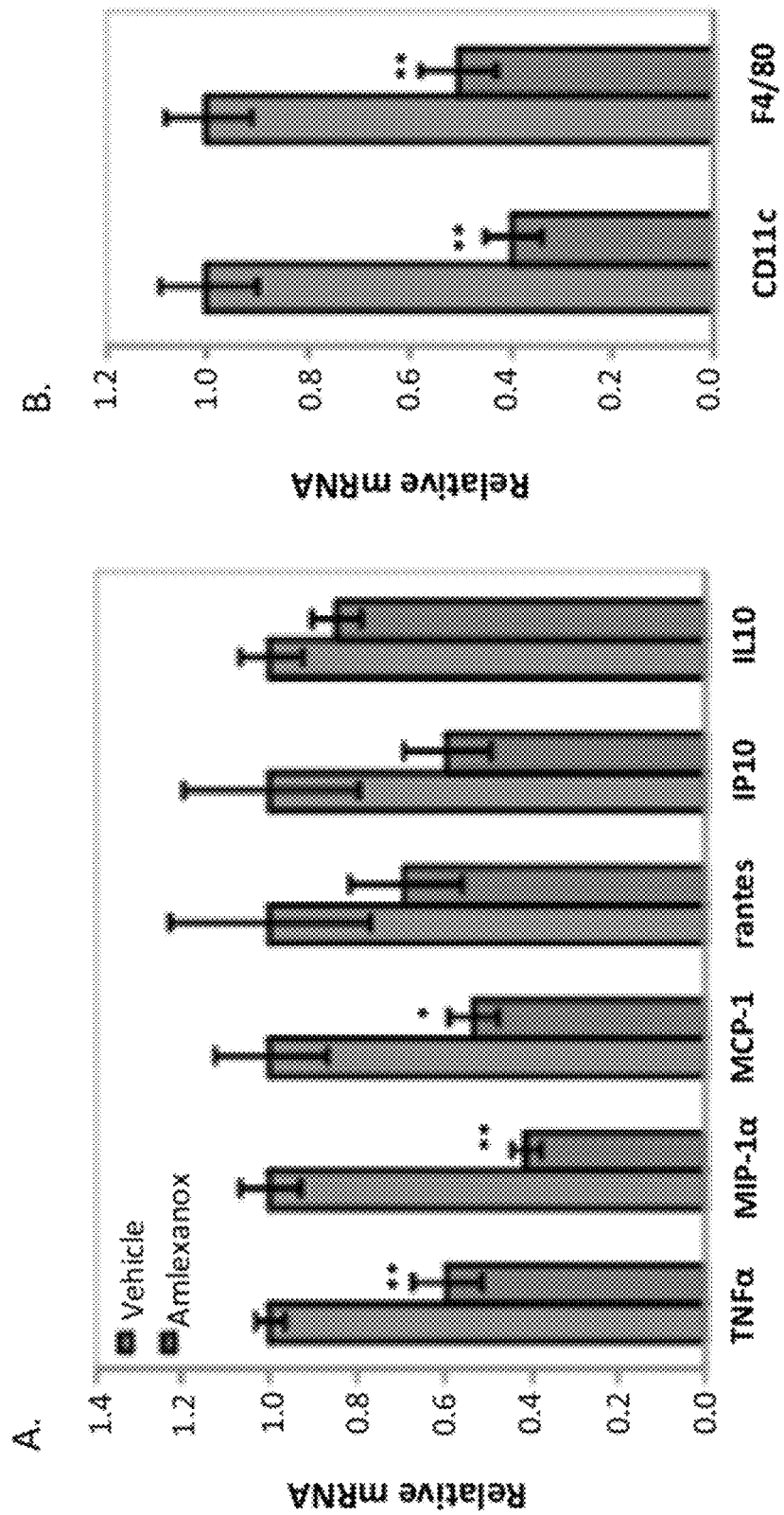
FIG. 12A shows relative mRNA levels for inflammatory genes expressed in epididymal adipose tissue of amlexanox-treated Ob/ob mice.
FIG. 12B shows relative mRNA levels for macrophage marker genes expressed in epididymal adipose tissue of amlexanox-treated Ob/ob mice.
Figure 13:
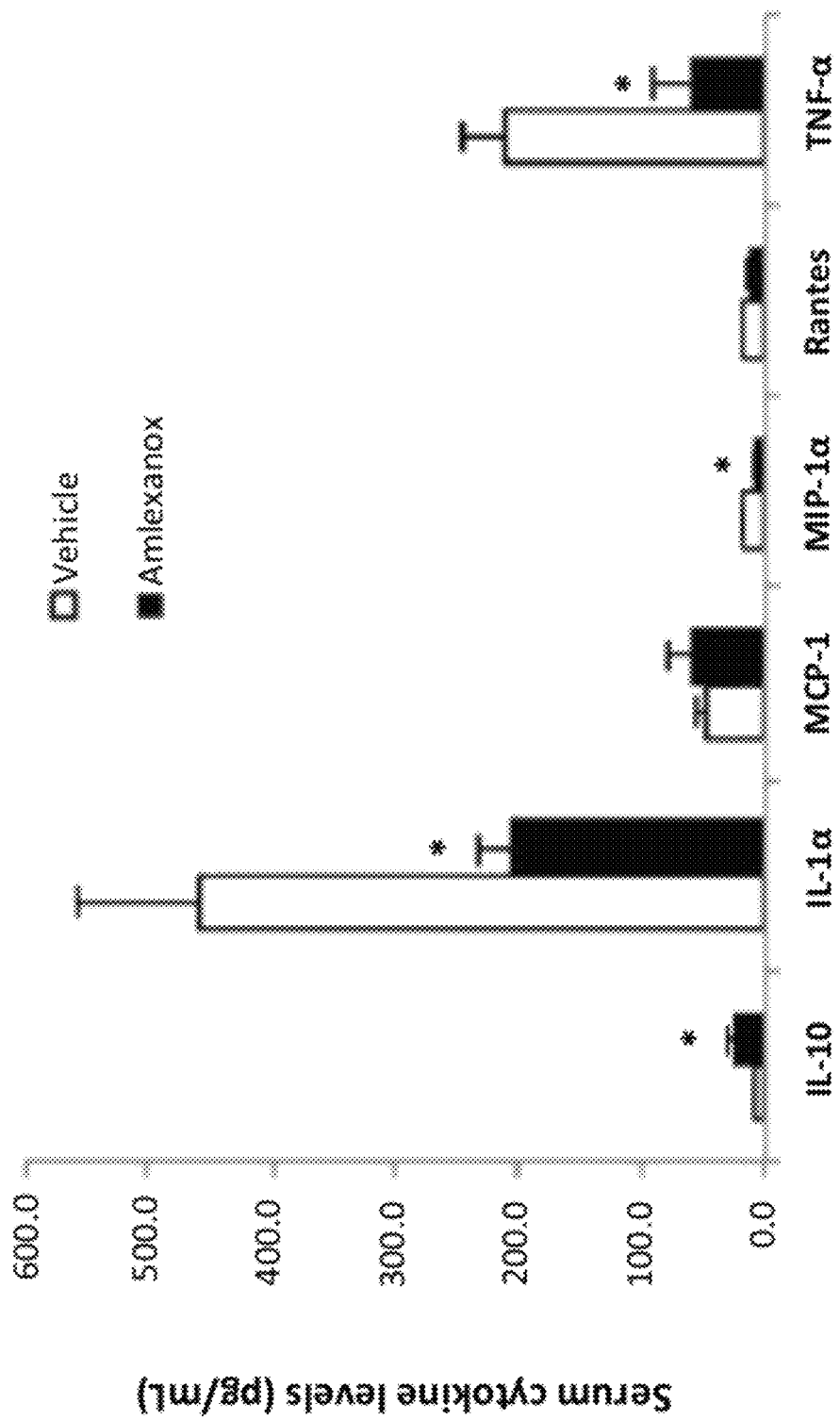
FIG. 13 shows a plot of serum cytokine levels in ob/ob mice gavaged with vehicle control (white bars) or 100 mg/kg amlexanox (black bars). (n=6 per group).

Cytokine levels in serum were also measured. As shown in FIG. 13, circulating levels of MCP-1 and Rantes were not significantly affected by amlexanox treatment, but the levels of TNFα, IL-1α, and MIP1α in serum were markedly reduced. In FIGS. 12 and 13, data marked with a single asterisk (*) have a p value of less than 0.05 and data marked with a double asterisk (**) have a p value of less than 0.01.

Figure 14:
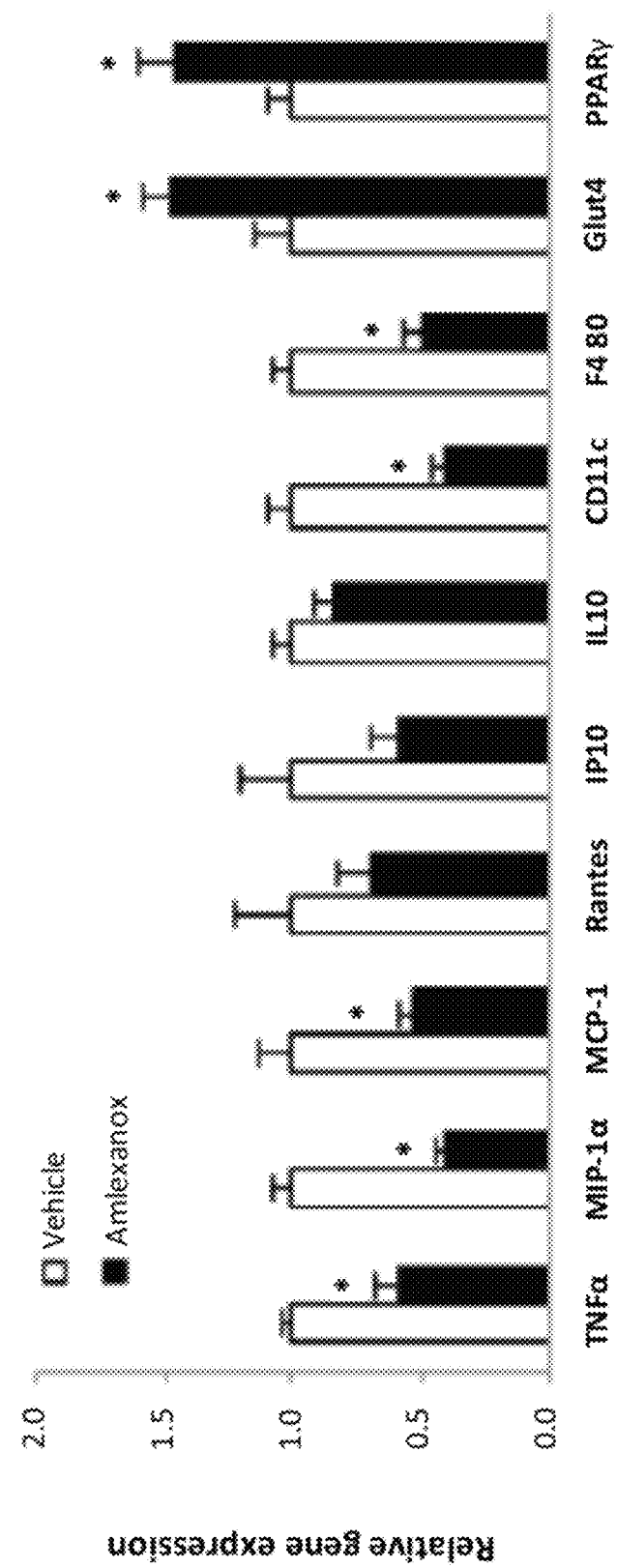
FIG. 14 shows expression of inflammatory genes and macrophage markers in white adipose tissue from ob/ob mice gavaged with vehicle control (white bars) or 100 mg/kg amlexanox (black bars) determined by Q-PCR (n=6 per group).
Figure 15:
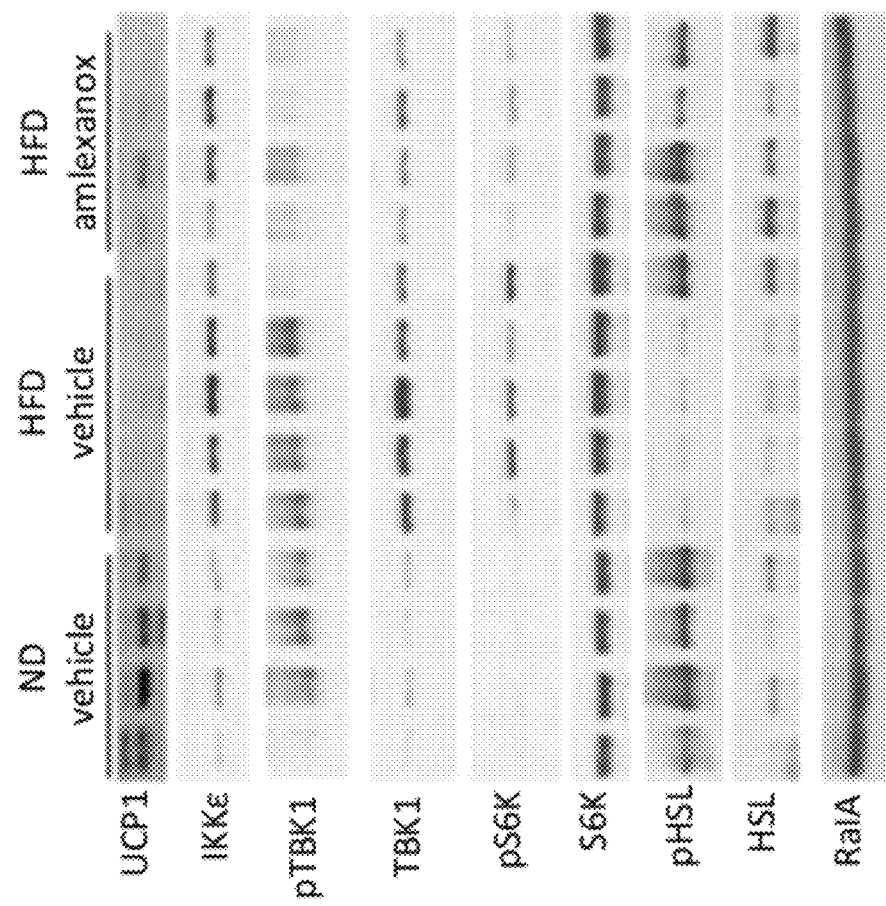
FIG. 15 shows a western blot of white adipose tissue protein levels of UCP1, non-canonical IKKs, and phosphorylation of S6K at threonine 389 and HSL at serine 562. RalA levels are shown as loading controls.

Additionally, serum levels of the antiinflammatory cytokine, IL-10 33, were elevated in amlexanox-treated mice compared to controls. Increased expression of fat cell-enriched proteins such as Glut4 and PPARγ, which are indicative of improved insulin sensitivity, was observed in WAT from amlexanox-treated mice (FIG. 14). The levels of UCP-1 protein were also increased in the adipose tissue of amlexanox-treated diet induced obese mice as compared to high fat diet vehicle-treated controls (FIG. 15).

Example 14

Figure 16:
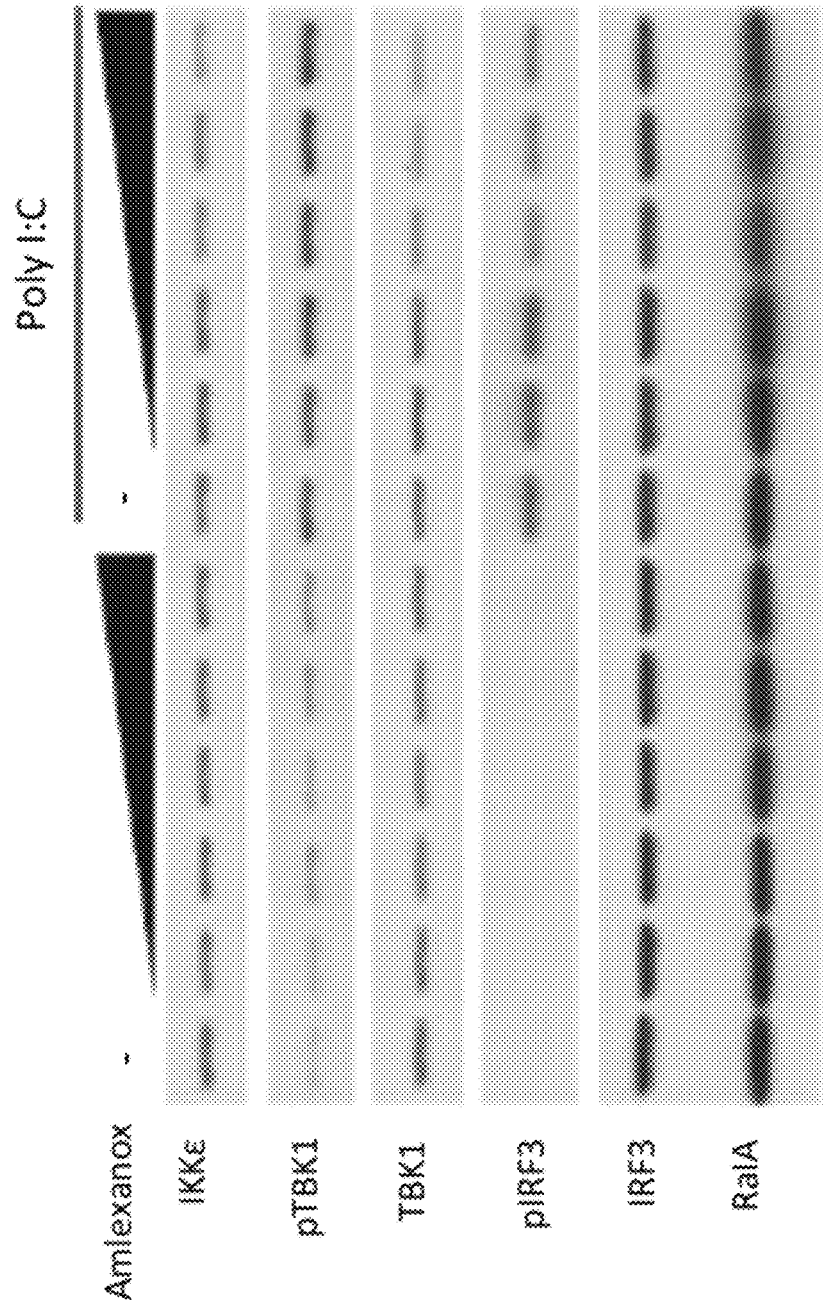
FIG. 16 shows a western blot of amlexanox-stimulated induction of TBK1 phosphorylation at serine 172 and inhibition of IRF3 phosphorylation at serine 396 in 3T3-L1 adipocytes treated with and without poly I:C. The amlexanox dose curve is a two-fold serial dilution with a highest concentration of 50 µM. Results were replicated in multiple experiments. RalA levels are shown as loading controls.
Figure 17:
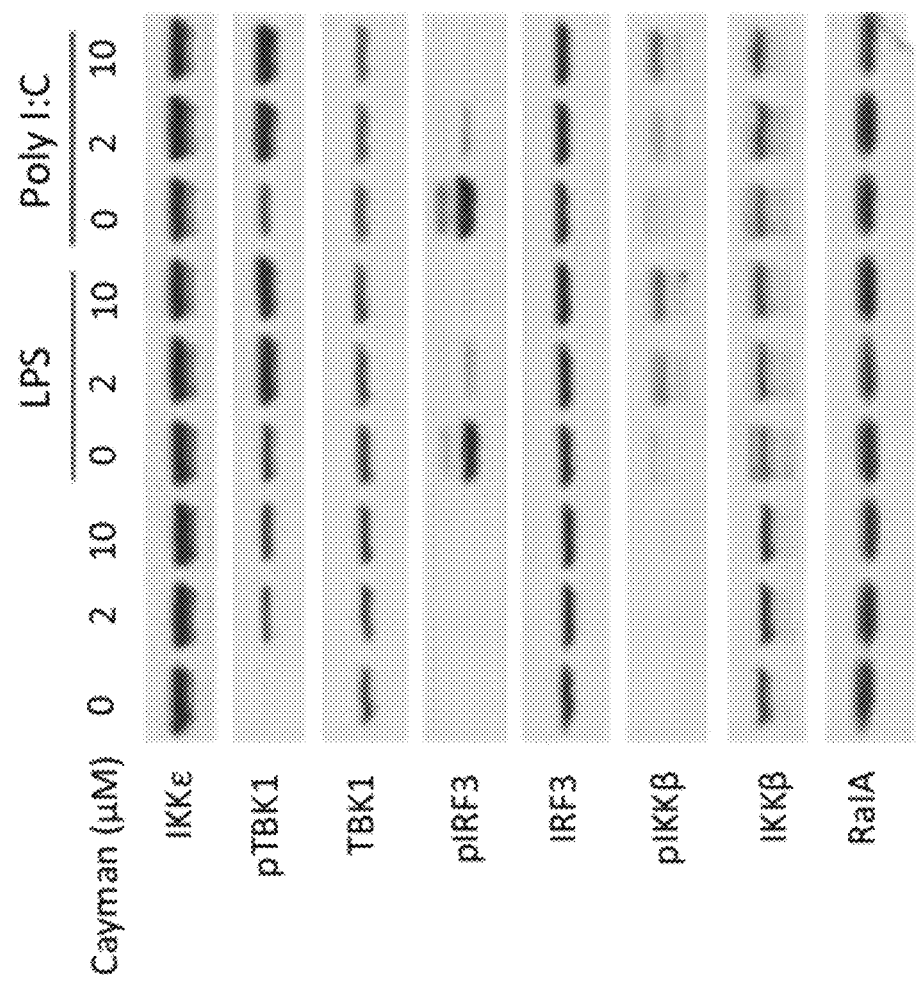
FIG. 17 is a western blot showing that cayman dependently reverses LPS and poly I:C induction of pIRF3, while inducing IKKβ and TBK1 phosphorylation in RAW264.7 cells. Results were replicated in multiple experiments. RalA levels are shown as loading controls.

During the development of embodiments of the technology provided herein, experiments demonstrated that addition of amlexanox to 3T3-L1 adipocytes produced the increased phosphorylation of TBK1 on serine 172, and blocked polyinosinic: polycytidylic acid (poly I:C)-stimulated phosphorylation of interferon responsive factor-3 (IRF3), a presumed substrate of IKKE and TBK1 26 (FIG. 16). Furthermore, addition of the previously identified IKKε/TBK1 inhibitor Cay-10576 (cayman) 27 to RAW264.7 macrophages stimulated with LPS or poly I:C also blocked the phosphorylation of IRF3, and stimulated phosphorylation of TBK1 on serine 172 (FIG. 17). This increased phosphorylation of TBK1 was also observed in peritoneal macrophages derived from IKKε knockout mice, and is likely due to blockade of feedback inhibition of the pathway 28, as evidenced by increased IKKβ phosphorylation in cayman-treated RAW cells.

Example 15

Figure 18:
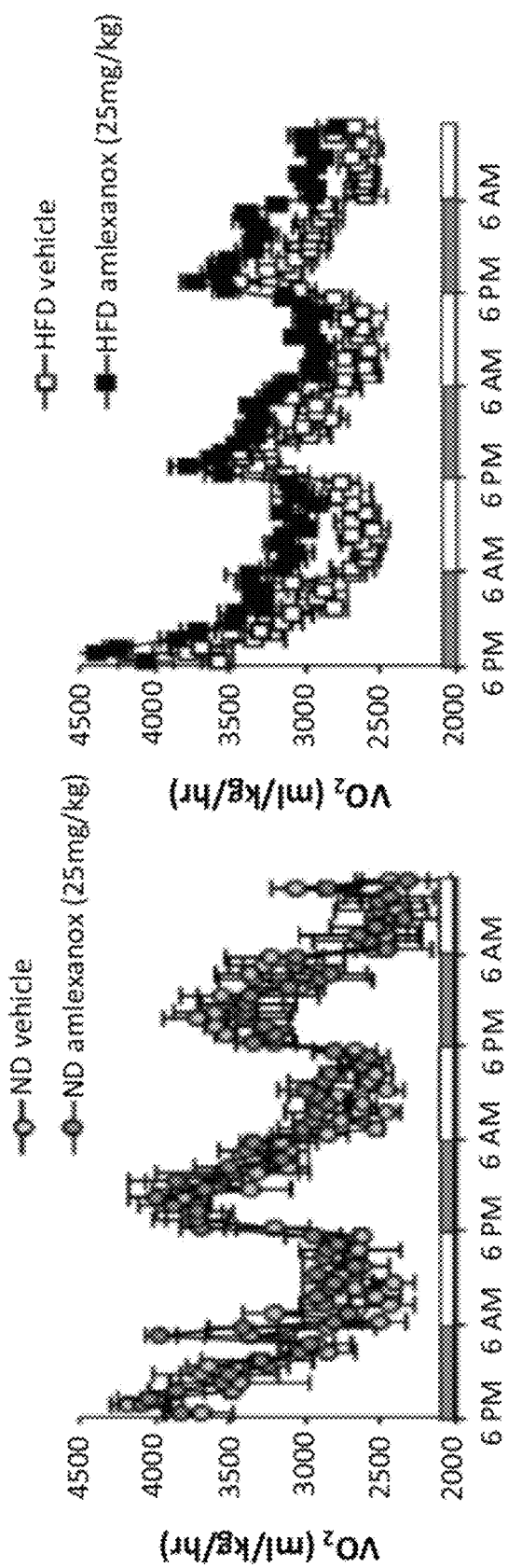
FIG. 18 is a plot of oxygen consumption ($VO_2$) versus time for mice treated with amlexanox; ND (left panel–light grey circles=vehicle, dark grey circles=25 mg/kg amlexanox) and HFD (right panel–white squares=vehicle, black squares=25 mg/kg amlexanox). (n=4 for ND groups, n=8 for HFD groups). HFD amlexanox treated mean values are significantly higher than HFD vehicle mean values during all three light and dark cycles, P value <0.05.
Figure 19:
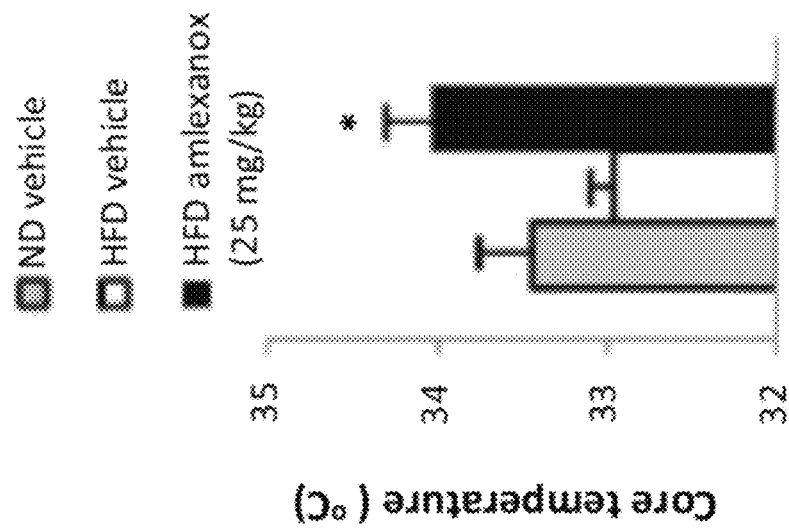
FIG. 19 is a plot showing core body temperature in ND fed mice gavaged with vehicle (grey bar), HFD fed mice gavaged with vehicle (white bar) and HFD fed mice gavaged with 25 mg/kg amlexanox (black bar). *P value<0.05 HFD vehicle control versus HFD amlexanox treated or ob/ob vehicle control versus ob/ob amlexanox treated. †P value<0.05 ND vehicle control versus HFD vehicle control.

During the development of embodiments of the technology provided herein, experiments demonstrated that amlexanox caused weight loss due to increased energy expenditure. Metabolic cages were used to monitor energy expenditure in diet induced obese mice treated with or without the drug. Four-week treatment with 25 mg/kg amlexanox resulted in significantly increased oxygen consumption as compared to vehicle control, consistent with an increase in energy expenditure (FIG. 18). Exhaled carbon dioxide was also significantly increased, such that the respiratory exchange ratio remained unchanged compared to control-treated mice. These data suggest that amlexanox induces an increase in thermogenesis; is support of this, rectal temperatures were measured (FIG. 19). Amlexanox treatment produced an approximate one-degree increase in body temperature compared to HFD vehicle treated mice.

Example 16

Figure 20:
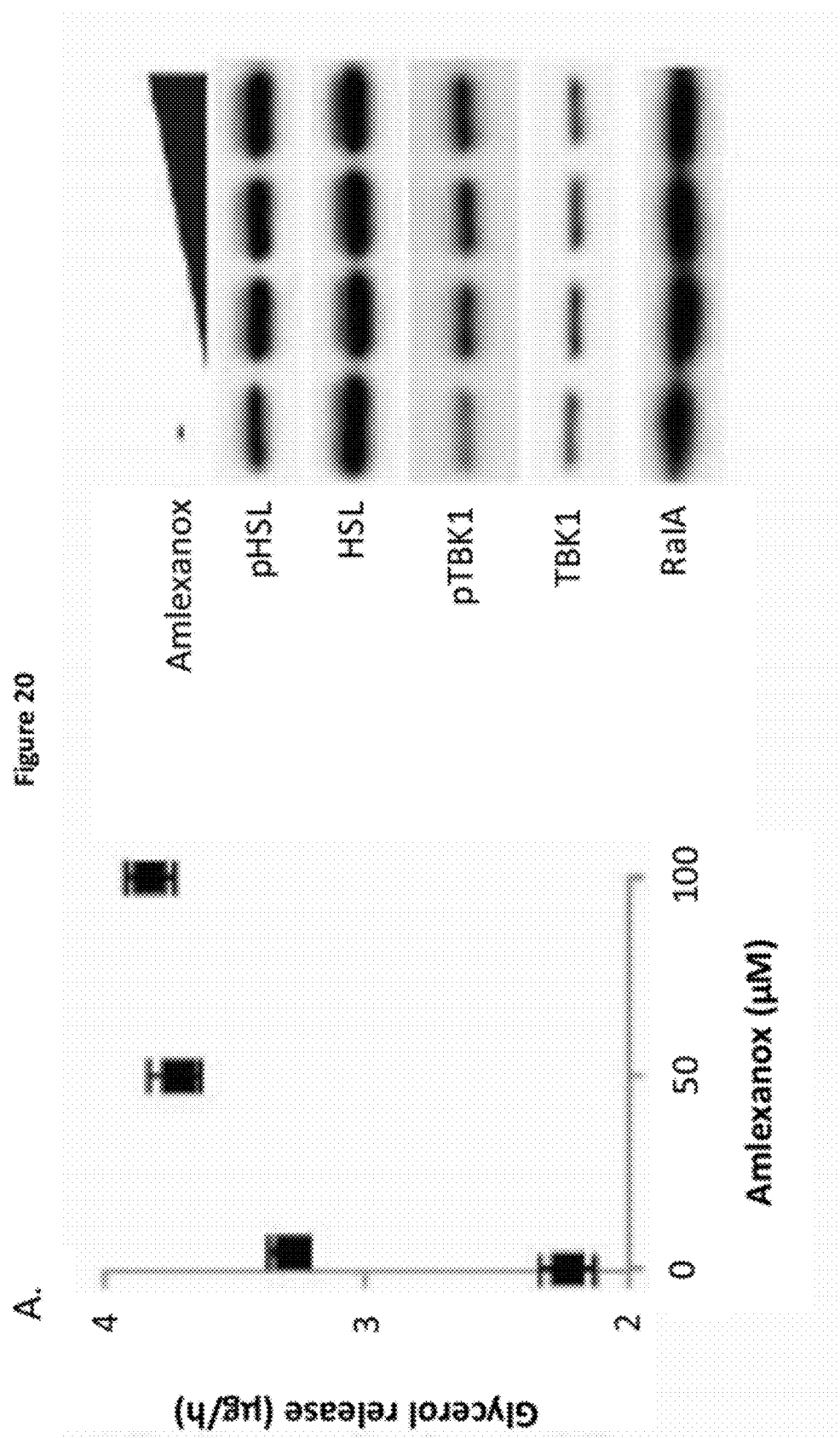
FIG. 20A is a plot showing an increased lipolytic rate in 3T3-L1 adipocytes treated with amlexanox, as measured by glycerol release (left panel). Corresponding HSL and TBK1 phosphorylation levels are shown in the right panel. RalA levels are shown as loading controls.
FIG. 20B is western blot showing that amlexanox partially restores forskolin-stimulated HSL phosphorylation at serine 660 in 3T3-L1 adipocytes chronically treated with TNFα. Phosphorylation of TBK1 at serine 172 is also restored by amlexanox treatment. Reduced PPARγ and increased IKKε protein levels are positive controls for TNFα effectiveness. Results were replicated in more than three experiments. RalA levels are shown as loading controls.

During the development of embodiments of the technology provided herein, experiments demonstrated that amlexanox administration regulates phosphorylation and promotes energy expenditure in adipose tissue. As described above, amlexanox is a specific inhibitor of IKKε and TBK1. To discern if the compound directly influences phosphorylation in vivo, a number of proteins known to undergo hyperphosphorylation in states of obesity were examined. Phosphorylation of proteins in the mTORC 1 pathway such as S6K were increased in response to a high fat diet; this increase was largely attenuated in amlexanox-treated diet induced mice (FIG. 15, compare pS6K, phosphorylated form to S6K, unphosphorylated form). The drug blocked high fat diet induction of IKKε protein and also prevented TBK1 phosphorylation in adipose tissue. This finding was consistent with the fact that overexpression of wild-type, but not kinase inactive TBK1, in cells increased the stimulation of S6K phosphorylation by insulin, while knockdown of IKKε or TBK1 in 3T3-L1 adipocytes reduced insulin-stimulated rS6 phosphorylation. In adipose tissue from high fat diet-fed mice, hormone sensitive lipase phosphorylation was reduced, consistent with the known desensitization of the β-adrenergic pathway in this tissue during obesity. Amlexanox treatment prevented the reduction in hormone sensitive lipase phosphorylation associated with high fat diet (FIG. 15, compare pHSL, phosphorylated form to HSL, unphosphorylated form). Moreover, treatment of 3T3-L1 adipocytes with amlexanox increased basal lipolytic rate and restored forskolin stimulated hormone sensitive lipase phosphorylation in cells that had been chronically treated with TNFα to induce IKKε and TBK1 activities (FIG. 20a and FIG. 20b). However, amlexanox did not affect the down regulation of PPARγ produced by treatment with TNFα.

Figure 21:
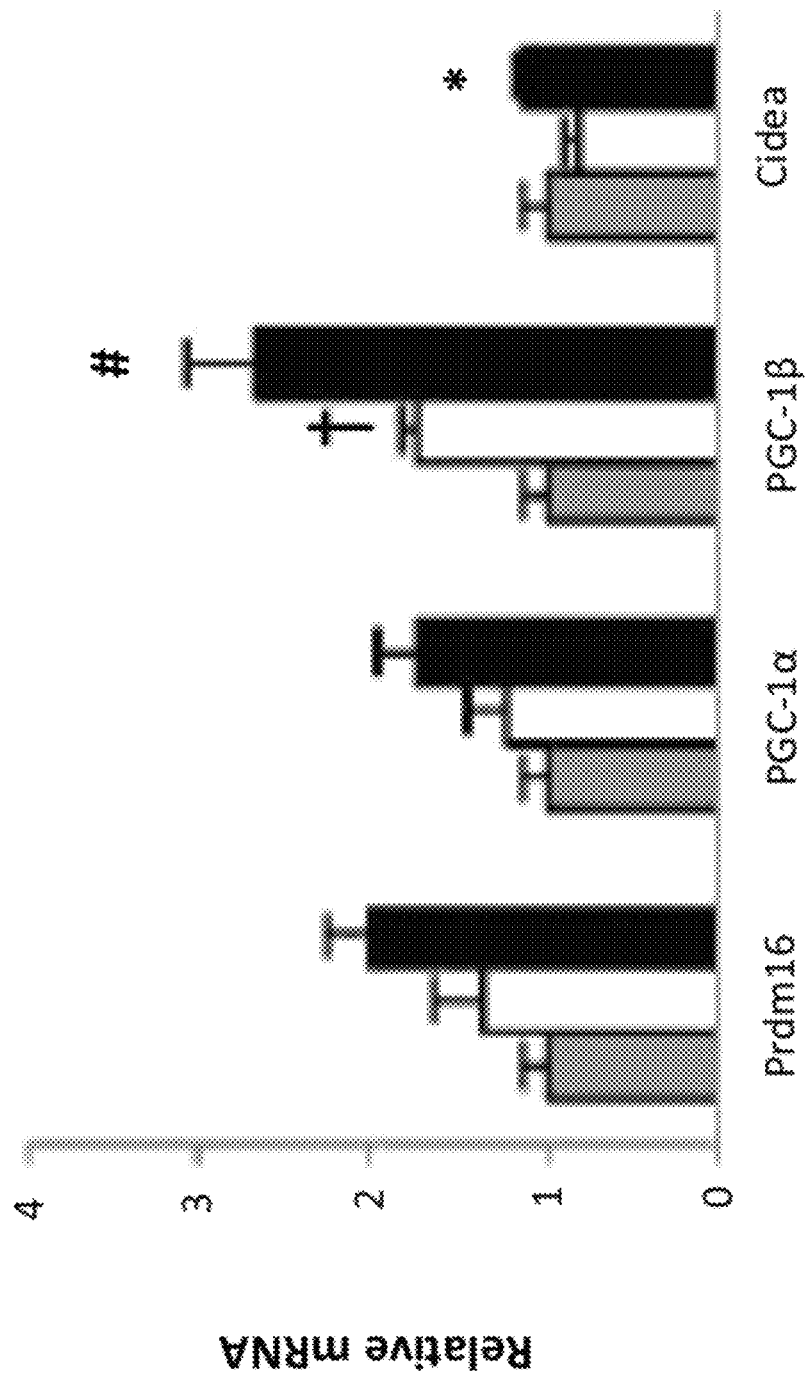
FIG. 21 is a plot showing the expression of BAT specific markers in BAT of treatment group determined by Q-PCR. Grey bars: ND vehicle control, white bars: high fat diet vehicle control; black bars: high fat diet gavaged daily with 25 mg/kg amlexanox (n=6 per group).
Figure 22:
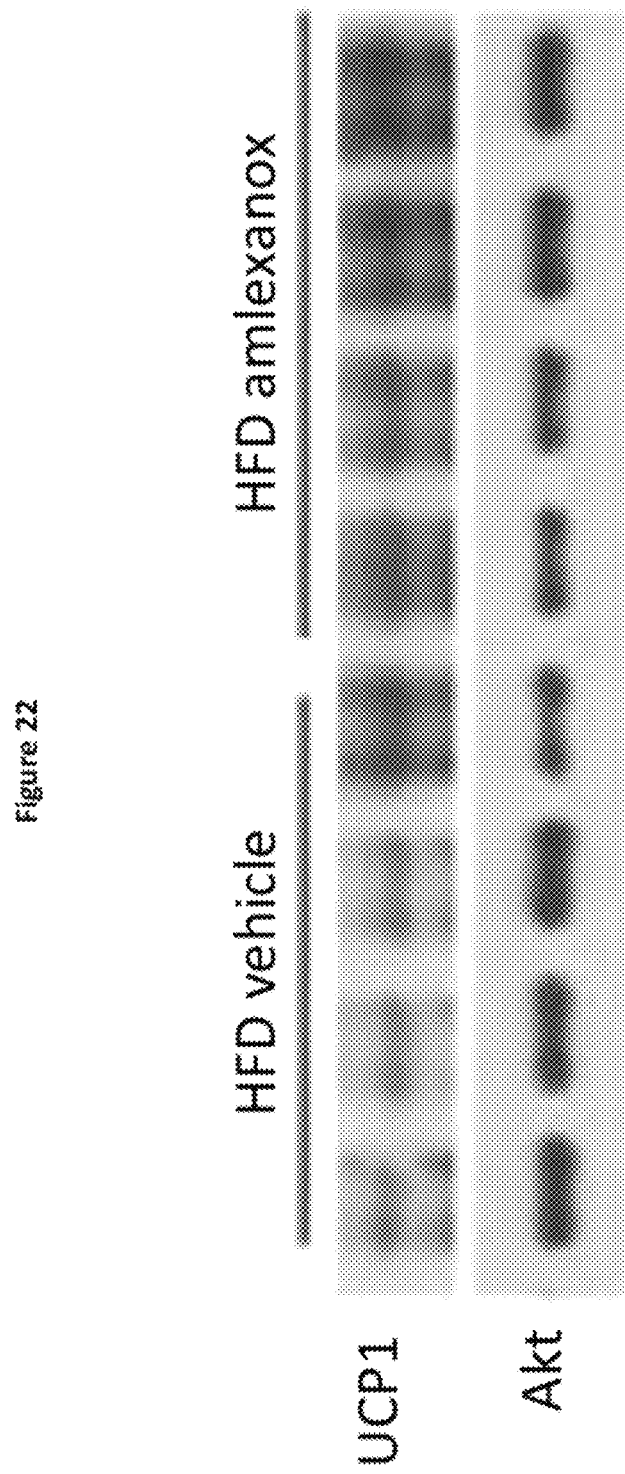
FIG. 22 is a western blot showing UCP-1 protein levels in BAT of treatment group. Akt levels are shown as loading controls. *P value<0.05 vehicle control versus amlexanox treated; #P value<0.1 HFD vehicle control versus HFD amlexanox treated; †P value<0.05 ND vehicle control versus HFD vehicle control.
Figure 23:
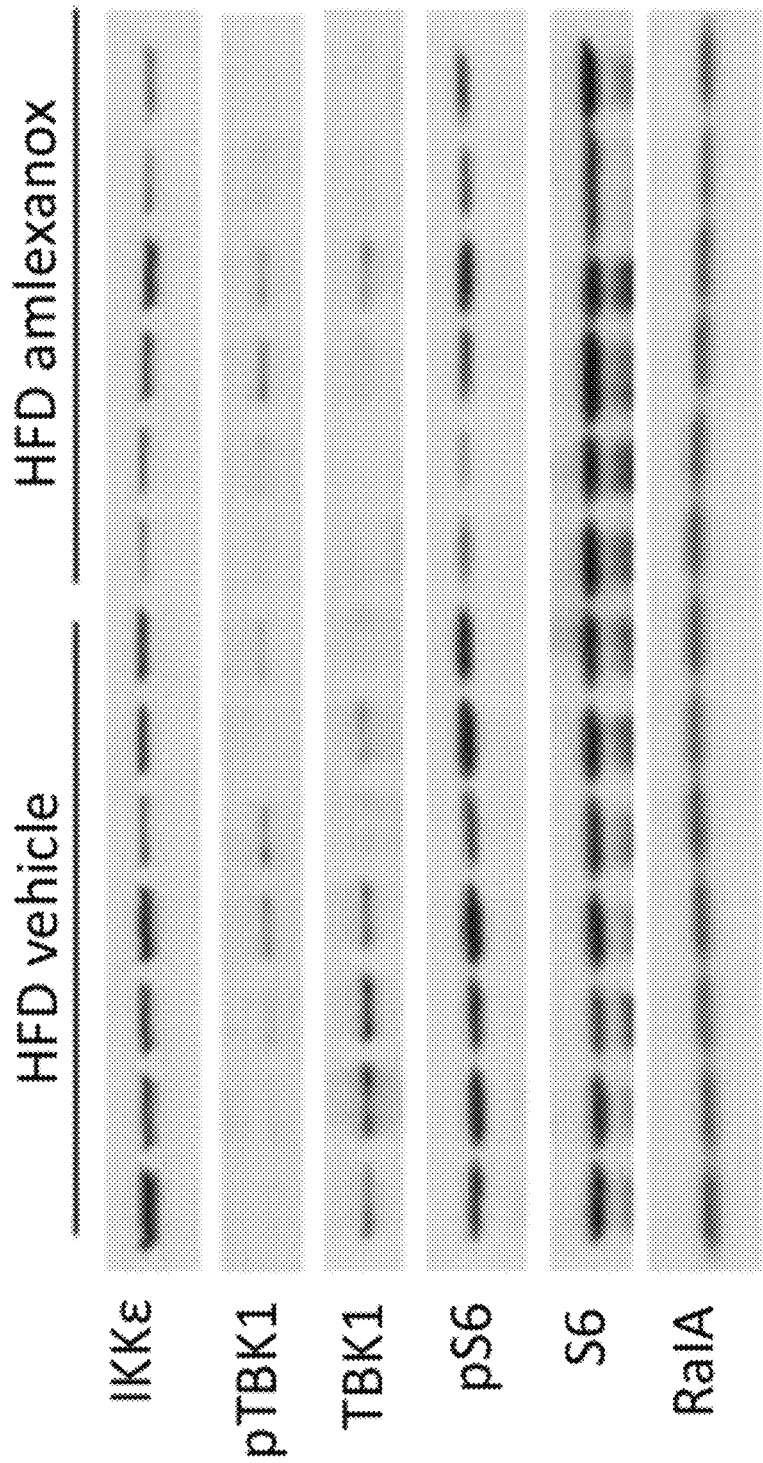
FIG. 23 is a western blot showing BAT protein levels of non-canonical IKKs, and phosphorylation of S6 at serine 235/236. RalA levels are shown as loading controls. Lipid oxidation rate in ex vivo BAT treated with amlexanox (black bar) or vehicle control (white bar). (n=6 per group). *P value<0.05 vehicle versus amlexanox treated.

Because brown adipose tissue (BAT) can play a major role in regulation of thermogenesis, the effects of the drug on this fat depot were examined. In control treated mice on high fat diet, brown adipose tissue accumulated large lipid droplets, and acquired some of the features of white fat. Brown fat reverted to its normal appearance in amlexanox-treated mice. When amlexanox treatment was stopped, lipids again accumulated in the BAT, reverting to the high fat diet phenotype of control obese mice. Expression of the brown fat-specific marker Cidea was increased in amlexanox-treated mice (FIG. 21). Additionally, amlexanox treatment increased levels of UCP1 protein in brown fat (FIG. 22), although there were no increases in mitochondrial genes compared to control. Additionally, amlexanox treatment reduced IKKε and TBK1 protein levels in BAT (FIG. 23). Reduced signaling through the mTORC1 pathway was also observed in BAT of amlexanox-treated mice as compared to controls. Ex vivo treatment with amlexanox acutely stimulated lipid oxidation in BAT explants, supporting a direct effect of amlexanox on energy expenditure (FIG. 24).

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in the relevant fields are intended to be within the scope of the following claims.

We claim:

1. A method of treating a human subject having a condition associated with obesity, insulin resistance, or hepatic steatosis by inhibiting TBK1 and/or IKKε consisting essentially of administering an orally effective amount of amlexanox, or a pharmaceutically acceptable salt thereof, to a human subject having a condition associated with obesity, insulin resistance, or hepatic steatosis, wherein the subject does not have an allergy, an aphthous ulcer, or bronchial asthma, and wherein the administering causes a reduction of body fat in the subject.

2. The method of claim 1, wherein the subject has or is at risk of experiencing obesity, diabetes, or insulin resistance.

3. The method of claim 2, wherein the diabetes is type II diabetes.

4. The method of claim 1, wherein the treatment results in increased glucose metabolism, reduction in body fat, lack of increase in body fat, increased insulin receptor signaling, decreased level of insulin receptor phosphorylation, reduction in or prevention of chronic inflammation in the liver, reduction in or prevention of chronic inflammation in adipose tissue, reduction in or prevention of hepatic steatosis, promotion of metabolic energy expenditure, reduction in circulating free fatty acids, or reduction in cholesterol.

5. The method of claim 1, wherein the subject has hepatic steatosis.

6. The method of claim 5, wherein the subject also has steatohepatitis.

7. The method of claim 1, wherein the subject is overweight or obese.

8. The method of claim 1, wherein the subject is not in need of tissue regeneration and/or is not suffering from tissue rejection.

9. The method of claim 1, wherein the subject does not have a cell proliferative disorder.

10. The method of claim 1, wherein the administering comprises administering amlexanox in combination with an additional therapeutic agent or medical intervention.

11. The method of claim 1, further comprising a step comprising testing the subject for a disease or condition selected from the group consisting of impaired insulin signaling, obesity, diabetes, insulin resistance, metabolic syndrome, hepatic steatosis, chronic liver inflammation, and chronic inflammation in adipose tissue.

12. The method of claim 11, further comprising the step of administering a second dose of amlexanox after the testing step.

13. The method of claim 1 wherein said orally effective amount of amlexanox, or a pharmaceutically acceptable salt thereof, is 25 mg/kg, and said subject has a condition associated with obesity.

* * * * *